US012594169B2

(12) United States Patent
Yadav et al.

(10) Patent No.: US 12,594,169 B2
(45) Date of Patent: Apr. 7, 2026

(54) EXPANDABLE INTERBODY

(71) Applicant: MiRus LLC, Marietta, GA (US)

(72) Inventors: Jay Yadav, Atlanta, GA (US); Noah Roth, Marietta, GA (US); Wayne Gray, Mableton, GA (US); Charles Brenner, Marietta, GA (US)

(73) Assignee: MiRus LLC, Marietta, GA (US)

( * ) Notice: Subject to any disclaimer, the term of this patent is extended or adjusted under 35 U.S.C. 154(b) by 0 days.

(21) Appl. No.: 19/196,538

(22) Filed: May 1, 2025

(65) Prior Publication Data

US 2025/0339285 A1     Nov. 6, 2025

Related U.S. Application Data

(63) Continuation-in-part of application No. 29/942,426, filed on May 15, 2024, and a continuation-in-part of application No. 29/942,443, filed on May 15, 2024.

(60) Provisional application No. 63/641,131, filed on May 1, 2024.

(51) Int. Cl.
*A61F 2/44*          (2006.01)

(52) U.S. Cl.
CPC ...... *A61F 2/447* (2013.01); *A61F 2220/0091* (2013.01); *A61F 2250/0004* (2013.01)

(58) Field of Classification Search
CPC .............. A61F 2/447; A61F 2220/0091; A61F 2250/0004
See application file for complete search history.

(56) References Cited

U.S. PATENT DOCUMENTS

2021/0275318 A1*   9/2021   Reimels ................ A61F 2/4611

* cited by examiner

*Primary Examiner* — Sameh R Boles
(74) *Attorney, Agent, or Firm* — UB Greensfelder LLP; Brian E. Turung

(57) ABSTRACT

An expandable interbody device used as a prosthesis during spinal surgery. The expandable interbody device is configured to be inserted into the space between spinal disks to provide stability. The expandable interbody device includes a drive block, a linkage block, a drive screw, a first endplate, a second endplate, and at least two linkages. Rotation of the drive screw causes movement of the linkage block relative to the drive block and/or movement of the first endplate relative to the second endplate.

30 Claims, 8 Drawing Sheets

1000

1000

1000

1000

1000

1000

1000

1000

1000

1000

EXPANDABLE INTERBODY

REFERENCED APPLICATIONS

The present disclosure claims priority on U.S. Provisional Patent Application Ser. No. 63/641,131 filed May 1, 2024, which is incorporated herein by reference.

The present disclosure is a continuation-in-part of U.S. Design patents application Ser. No. 29/942,426 filed May 15, 2024 and 29/942,443 filed May 15, 2024, which are both incorporated herein by reference.

FIELD OF DISCLOSURE

An expandable interbody device that can be used as a prosthesis during spinal surgery. The expandable interbody device is configured to be inserted into the space between spinal disks to provide stability. The expandable interbody device can be introduced between vertebrae of a patient's spine for fixation with bone to immobilize the joint as part of a surgical treatment.

BACKGROUND OF THE DISCLOSURE

Intervertebral fusion devices for the cervical and lumbar spine have been used for many years. These devices are originally inserted into a disc space after the coring out a bone graft from the hip. This technique currently not commonly practice due to disadvantages such as lengthy operation times, destruction of a large portion of the disc space, high risk of nerve injury, and hip pain after harvesting the bone graft.

A current device commonly used to perform the intervertebral portion of an intervertebral body fusion is an intervertebral body fusion device and a distraction device. One such device is illustrated in US 2022/0168116, which is incorporated herein by reference.

The intervertebral body fusion device can be implanted as a standalone device or implanted in combination with other devices such as pedicle screws and rods. The intervertebral body fusion device distracts a collapsed disc, decompresses the nerve root, and allows load sharing to enhance bone formation. The intervertebral body fusion device is configured to be small enough to allow implantation with minimal retraction and pulling on nerves.

In a typical intervertebral body fusion procedure, a portion of the intervertebral disc is first removed from between the vertebral bodies. The distraction device is then inserted into the cleared space to enlarge the disc space and the vertebral bodies are separated by the distraction device. Thereafter, the intervertebral fusion device is inserted into the distracted space.

The present disclosure is directed to an improved expandable interbody device.

SUMMARY OF DISCLOSURE

The present disclosure is directed to an expandable interbody device that can be used as a prosthesis used during spinal surgery. The expandable interbody device is configured to be inserted into the space between spinal disks to provide stability. The expandable interbody device can be introduced between vertebrae of a patient's spine (e.g., in the disk space between adjacent vertebrae) for fixation with bone to immobilize the joint as part of a surgical treatment.

In one non-limiting aspect of the disclosure, the expandable interbody device includes a drive block, a linkage block, a drive screw, a first endplate, a second endplate, and a first set of linkages wherein the first set of linkages includes first and second linkages.

In another and/or alternative non-limiting aspect of the disclosure, the drive block optionally at least partially forms or includes a drive block opening, and the linkage block optionally at least partially forms or includes a linkage block opening. The drive screw is rotatably coupled at least partially in the drive block opening or linkage block opening and is threadingly disposed within the other of the linkage block opening or the drive block opening. In one non-limiting embodiment, a) the drive block includes a drive block opening and a head of the drive screw is rotatably coupled in a portion of the drive block opening, b) the head of the drive screw that is located in the drive block opening is not threadedly coupled to the drive block, c) during rotation of the drive screw, the head of the drive screw is able to rotate within the drive block opening, but does move or moves less than 5% (e.g., 0-5% and all values and ranges therebetween) the longitudinal length of the drive block opening, d) the linkage block includes a linkage block opening and at least a portion of the linkage block opening includes threading, e) the body of the drive screw includes threading that is threadedly connected to at least a portion of the threading in the linkage block opening, f) during rotation of the drive screw a portion of the body of the drive screw moves with the linkable block opening along a longitudinal axis of the linkage block opening, and g) during rotation of the drive screw a distance between the drive block opening and the linkage block opening is caused to change. In another non-limiting embodiment, a) the drive block includes a drive block opening and at least a portion of the drive block opening includes threading, b) a head of the drive screw is threadedly coupled to a portion of the threading in the drive block opening, c) during rotation of the drive screw, the head of the drive screw is able to rotate within the drive block opening, and moves with the drive block opening along a longitudinal axis of the drive block opening, d) the linkage block includes a linkage block opening, e) the body of the drive screw is rotatably connected to at least a portion of the linkage block opening, f) during rotation of the drive screw, a portion of the body of the drive screw is able to rotate within the linkage drive block opening, but does move or moves no more or less than 5% (e.g., 0-5% and all values and ranges therebetween) the longitudinal length of the linkage block opening, and g) during rotation of the drive screw a distance between the drive block opening and the linkage block opening is caused to change. In another non-limiting embodiment, the head of the drive screw and the drive block opening of the drive block are configured such that the proximal end of the head of the drive screw that is located farthest from the body of the drive screw always remains within the drive block opening of the drive block during the full expansion and fully contraction of the expandable interbody device. In another non-limiting embodiment, the head of the drive screw and the drive block opening of the drive block are configured such that a) the head of the drive screw includes a rib about a portion of all of the outer circumference of the head and the rib is position in a slot in a portion or all of an inner circumference of the drive block opening so that the head of the drive screw can rotate in drive block open, but not move along the longitudinal length of the drive block opening during the rotation of the drive screw, and/or b) the head of the drive screw includes a slot about a portion of all of the outer circumference of the head and the slot is position in a rib in a portion or all of an inner circumference of the drive block opening so that the head of the drive screw can rotate in drive block open, but not move along the longitudinal length of the drive block opening during the rotation of the drive screw. As can be appreciated, more than one slot/rib arrangement can be used. As can also be appreciated, other or additional arrangements can be used to allow the head of the drive screw to rotate within the drive block opening, and the head of the drive screw not move along the longitudinal length of the drive block opening during the rotation of the drive screw.

In another and/or alternative non-limiting aspect of the disclosure, a first end portion of the first linkage on the first set of linkages is rotatably coupled the linkage block and the second end portion of the first linkage on the first set of linkages engages the first endplate, and a first end portion of the second linkage on the first set of linkages is rotatably coupled the linkage block and the second end portion of the second linkage on the first set of linkages engages the second endplate. In one embodiment, rotation of the drive screw causes movement of the linkage block relative to the drive block and movement of the first endplate relative to the second endplate. In another non-limiting embodiment, the second end portion of the first linkage on the first set of linkages includes a first linkage pin that is used to a) facilitate in the movement of the first endplate when the drive screw is rotated to cause a distance between the drive block opening and the linkage block opening is caused to change, b) facilitates in maintaining the engagement of the second end portion of the first linkage and/or the first linkage pin to the first endplate during movement of the first endplate when the drive screw is rotated to cause a distance between the drive block opening and the linkage block opening is caused to change, c) rotatably engage the second end portion of the first linkage on the first set of linkages to the first endplate, but not rotatably secured and/or attached to the first endplate, and/or d) rotatably attach the second end portion of the first linkage on the first set of linkages to the first endplate. In another non-limiting embodiment, the second end portion of the second linkage on the first set of linkages includes a second linkage pin that is used to a) facilitate in the movement of the second endplate when the drive screw is rotated to cause a distance between the drive block opening and the linkage block opening is caused to change, b) facilitates in maintaining the engagement of the second end portion of the second linkage and/or the second linkage pin to the second endplate during movement of the second endplate when the drive screw is rotated to cause a distance between the drive block opening and the linkage block opening is caused to change, c) rotatably engage the second end portion of the second linkage on the first set of linkages to the second endplate, but not rotatably secured and/or attached to the second endplate, and/or d) rotatably attach the second end portion of the second linkage on the first set of linkages to the second endplate. In one specific arrangement, the second end portion of the first and second linkage on the first set of linkages includes a first linkage pin that is used to a) facilitate in the movement of the first endplate and second endplate respectively when the drive screw is rotated to cause a distance between the drive block opening and the linkage block opening is caused to change, b) facilitate in maintaining the engagement of the second end portion of the first and second linkages and the first and second linkage pins to the first and second endplates respectively during movement of the first and second endplates when the drive screw is rotated to cause a distance between the drive block opening and the linkage block opening is caused to change, c) rotatably engage the second end portion of the first and second linkages on the first set of linkages to the first and second endplates respectively, but not rotatably secured and/or attached to the first and second endplates respectively.

In another and/or alternative non-limiting aspect of the disclosure, the expandable interbody device further includes a second set of linkages that includes first and second linkages, and wherein the second set of linkages are positioned on the opposite side of the expandable interbody device from the expandable interbody device, and the first end portion of the first linkage on the second set of linkages is rotatably coupled the linkage block and the second end portion of the first linkage on the second set of linkages engages the first endplate, and a first end portion of the second linkage on the second set of linkages is rotatably coupled the linkage block and the second end portion of the second linkage on the second set of linkages engages the second endplate. In one non-limiting arrangement, the second set of linkages is configured to the same or similar to the first set of linkages and performs the same or similar function as the first set of linkages during movement of the first and second endplates when the drive screw is rotated to cause a distance between the drive block opening and the linkage block opening is caused to change.

In another and/or alternative non-limiting aspect of the disclosure, the first portion of the first and second linkages of the first and/or second set of linkages are rotatably coupled to the linkage block along the same rotation axis.

In another and/or alternative non-limiting aspect of the disclosure, the first portion of the first and second linkages of the first and/or second set of linkages are rotatably coupled to the linkage block along a different rotation axis.

In another and/or alternative non-limiting aspect of the disclosure, the drive block optionally includes a slot region that is positioned distal to the drive block opening. In one non-limiting arrangement, the drive block includes top and bottom slots. The slots can optionally be used to facilitate in bone and tissue growth within the expandable interbody device after the expandable interbody device has been implanted in a patient.

In another and/or alternative non-limiting aspect of the disclosure, the linkage block includes a linkage housing and a linkage bar wherein the linkage bar includes end flanges. In one non-limiting arrangement, the linkage housing is configured to receive at least a portion of the linkage bar. In another non-limiting arrangement, both the linkage housing and the linkage bar include a screw opening and when the linkage bar is positioned in the linkage housing, and wherein the screw openings of the linkage bar and the linkage housing are configured to align such that at least a portion of the drive screw body is positioned through both of the screw openings of the linkage bar and the linkage housing. In another non-limiting arrangement, the screw opening in the linkage bar and/or linkage housing includes threading that is configured to engage threading on the body of the drive screw. In another non-limiting arrangement, the first and/or second linkages of the first set of linkages are rotatably or pivotally connected to at least one of the end flanges of the linkage bar, and the first and/or second linkages of the optional second set of linkages are rotatably or pivotally connected to at least one of the end flanges of the linkage bar. In one non-limiting specific arrangement, the first and second linkages of the first set of linkages are rotatably or pivotally connected to one of the end flanges of the linkage bar, and the first and second linkages of the optional second set of linkages are rotatably or pivotally connected to the other end flange of the linkage bar.

In another and/or alternative non-limiting aspect of the disclosure, the linkage block opening optionally includes threading that is located distally of the head of the drive screw when the head of the drive screw is rotatably secured in drive block opening. The threading in the linkage block opening is configured to receive threading on an insertion tool that is configured to be used to insert the expandable interbody device into a treatment area (e.g., foot, ankle, wrist, hand, spine, etc.), and thereafter the insertion tool removed from the expandable interbody device. The insertion tool can be optionally configured to engage the head of the drive screw and be used to rotate the head of the drive screw.

In another and/or alternative non-limiting aspect of the disclosure, the expandable interbody device optionally includes one or more graft windows, cavities and/or slots. The one or more graft windows, cavities and/or slots, when used, are configured to facilitate in bone and/or tissue growth on the expandable interbody device after the expandable interbody device has been implanted at a treatment site.

In another and/or alternative non-limiting aspect of the disclosure, the expandable interbody device optionally includes first and/or second endplates that include a micro-textured surface and/or one or more teeth.

In another and/or alternative non-limiting aspect of the disclosure, the expandable interbody device optionally includes first and second endplates that include planar top surfaces that do not lie within the same plane when the expandable interbody device is in the fully expanded position. In one non-limiting arrangement, the angle formed by the plane of 50-100% (and all values and ranges therebetween) of the top surface of the first and second endplates is about 10°-60° (and all values and ranges therebetween) when the expandable interbody device is in the fully expanded position.

In another and/or alternative non-limiting aspect of the disclosure, the expandable interbody device optionally includes first and second endplates that include planar top surfaces that lie within or closely within the same plane when the expandable interbody device is in the fully contracted position. In one non-limiting arrangement, the angle formed by the plane of 50-100% (and all values and ranges therebetween) of the top surface of the first and second endplates is about 0°-10° (and all values and ranges therebetween) when the expandable interbody device is in the fully contracted position. In one non-limiting arrangement, the angle formed by the plane of 50-100% (and all values and ranges therebetween) of the top surface of the first and/or second endplates relative to the central axis of the drive block is about 0°-5° (and all values and ranges therebetween) when the expandable interbody device is in the fully contracted position.

In another non-limiting embodiment, the expandable interbody device is optionally configured such that the front and rear ends of the first and second endplates do not contact one another as the expandable interbody device moves from the fully open to the fully closed position.

In another non-limiting embodiment, the expandable interbody device is optionally configured such that the drive block and the first and/or second endplates include one or more engagement members (e.g., slot, protrusion, rib, rail, groove, etc.) that are configured to slidably engage with respect to one another so as to facilitate in a) guiding of movement of the first and/or second endplates relative to the drive block as the expandable interbody device moves from the fully closed or collapsed position to the fully open or expanded position, and/or b) inhibiting or prevent over expansion of the first and/or second endplates relative to the drive block as the expandable interbody device moves from the fully closed or collapsed position to the fully open or expanded position. In one non-limiting arrangement, the drive block includes one or more guide flanges on one or both sides of the drive block, and the first and/or second endplates include one or more guide slot on one or both sides of the first and/or second endplates, and where the guide slot is configured to slidably receive at least a portion of a guide flange. In another non-limiting arrangement, the drive block includes one or more guide slots on one or both sides of the drive block, and the first and/or second endplates include one or more guide flanges on one or both sides of the first and/or second endplates, and where the guide slot is configured to slidably receive at least a portion of a guide flange. In another non-limiting arrangement, one or more of the guide slots and one or more of the guide flanges has an arcuate shape or profile. In another non-limiting arrangement, the drive block includes one or more guide flanges and/or guide slots on each side of the drive block, and the location of one of the guide flanges and/or guide slots on one side of the drive block is spaced a different distance from a proximal end of the drive block than the location of one of the guide flanges and/or guide slots on the other side of the drive block. In another non-limiting arrangement, the drive block includes first and second guide flanges wherein the first guide flange is located on one side of the drive black and the second guide flange is located on the opposite side of the drive block, and the first endplate includes one guide slot on one side of the first endplate, and the second endplate includes one guide slot on one side of the second endplate, and the guide slot on the first endplate slidably engages the first glide flange, and the guide slot on the second endplate slidably engages the second glide flange, and the spacing of the first guide flange from the proximal end of the drive block is optionally different from the spacing of the second glide flange from the proximal end of the drive block, and the first guide flange and the guide slot on the first endplate optionally have an arcuate shape or profile, and the second guide flange and the guide slot on the second endplate optionally have an arcuate shape or profile.

In another non-limiting embodiment, the expandable interbody device is optionally configured such that the drive block and/or the linkage block move along a longitudinal axis of the first and/or second endplates as the expandable interbody device moves from the fully closed or collapsed position to the fully open or expanded position. In one non-limiting arrangement, both the drive block and the linkage block move along a longitudinal axis of the first and/or second endplates as the expandable interbody device moves from the fully closed or collapsed position to the fully open or expanded position. In another non-limiting arrangement, both the drive block and the linkage block move along a longitudinal axis of the first and/or second endplates as the expandable interbody device moves from the fully closed or collapsed position to the fully open or expanded position, and the linkage block moves a greater distance along the longitudinal axis of the first and/or second endplates than the drive block as the expandable interbody device moves from the fully closed or collapsed position to the fully open or expanded position.

In another non-limiting embodiment, the expandable interbody device is optionally configured such that the both the proximal and distal ends of the first and second endplates move away from one another as the expandable interbody device moves from the fully closed or collapsed position to the fully open or expanded position. In one non-limiting arrangement, the distal ends of the first and second endplates move away from one another a greater distance than the proximal ends of the first and second endplates as the expandable interbody device moves from the fully closed or collapsed position to the fully open or expanded position.

In another non-limiting embodiment, the expandable interbody device is optionally configured such that the first and second endplates includes an opening through the top and bottom surfaces of the first and second endplates, and the drive block includes an opening through the top and bottom surfaces of the drive block, and the openings in the first and second endplates and the opening in the drive block are at least partially aligned with one another as the expandable interbody device is in the fully closed or collapsed position and the fully open or expanded position, and also when the expandable interbody device moves from the fully closed or collapsed position to the fully open or expanded position. The size of the opening in the top and bottom surfaces of the first and second endplates is at least 10% (e.g., 10-70% and all values and ranges therebetween) of the top surface area of the top and bottom surfaces of the first and second endplates, and the size of the opening in the top and bottom surfaces of the drive block is at least 10% (e.g., 10-90% and all values and ranges therebetween) of the top surface area of the drive block.

In another non-limiting embodiment, the expandable interbody device is optionally configured such that the proximal end of the drive block includes pin slots, and the proximal end of the first and/or second endplates includes a plate slot, and wherein the pin slot and a the plate slot is configured to receive a guide pin that is configured to limit the amount of movement of the proximal end of the drive block relative to the first and/or second endplates as the expandable interbody device moves from the fully closed or collapsed position to the fully open or expanded position. In one non-limiting arrangement, both the first and second endplates includes a plate slot having an elongated shape such a guide pin can move in a transverse axis in the plate slot relative to the longitudinal axis of the first and second endplates.

In another and/or alternative non-limiting aspect of the disclosure, one or more or all of the components of the expandable interbody device is partially or fully formed of a metal alloy. In one non-limiting embodiment, a portion or all of the one or more or all of the components of the expandable interbody device is formed of a metal alloy selected from a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) refractory metal alloy, or l) metal alloy that includes at least 5 atomic weight percent (awt. %) or atomic percent (awt. %) rhenium (e.g., 5-99 awt. % rhenium and all values and ranges therebetween). As used herein, atomic weight percent (awt. %) or atomic percent (awt. %) are used interchangeably. As defined herein, the weight percentage (wt. %) of an element is the weight of that element measured in the sample divided by the weight of all elements in the sample multiplied by 100. The atomic percentage or atomic weight percent (awt. %) is the number of atoms of that element, at that weight percentage, divided by the total number of atoms in the sample multiplied by 100. The use of the terms weight percentage (wt. %) and atomic percentage or atomic weight percentage (awt. %) are two ways of referring to metallic alloy and its constituents. As defined herein, a stainless-steel alloy (SS alloy) includes 10-28 wt. % (weight percent) chromium, 0-35 wt. % nickel, 0-4 wt. % molybdenum, 0-2 wt. % manganese, 0-0.75 wt. % silicon, 0-0.3 wt. % carbon, 0-5 wt. % titanium, 0-10 wt. % niobium, 0-5 wt. % copper, 0-4 wt. % aluminum, 0-10 wt. % tantalum, 0-1 wt. % Se, 0-2 wt. % vanadium, 0-2 wt. % tungsten, and at least 50 wt. % iron. One non-limiting stainless-steel alloy is 316L stainless-steel that includes 17-19 wt. % chromium, 13-15 wt. % nickel, 2-4 wt. % molybdenum, 2 wt. % max manganese, 0.75 wt. % max silicon, 0.03 wt. % max carbon, balance iron. As defined herein, a cobalt-chromium alloy (CoCr alloy) includes 15-32 wt. % chromium, 1-38 wt. % nickel, 2-18 wt. % molybdenum, 0-18 wt. % iron, 0-1 wt. % titanium, 0-0.15 wt. % manganese, 0-0.15 wt. % silver, 0-0.25 wt. % carbon, 0-16 wt. % tungsten, 0-2 wt. % silicon, 0-2 wt. % aluminum, 0-1 wt. % iron, 30-68 wt. % cobalt, 0-0.1 wt. % boron, 0-0.15 wt. % silver, and 0-2 wt. % titanium. One type of cobalt-chromium alloy is MP35N alloy that includes 18-22 wt. % chromium, 32-38 wt. % nickel, 8-12 wt. % molybdenum, 0-2 wt. % iron, 0-0.5 wt. % silicon, 0-0.5 wt. % manganese, 0-0.2 wt. % carbon, 0-2 wt. % titanium, 0-0.1 wt. %, 0-0.1 wt. % boron, 0-0.15 wt. % silver, and balance cobalt. Two other types of cobalt-chromium alloy are Phynox and Elgiloy alloy that include 38-42 wt. % cobalt, 18-22 wt. % chromium, 14-18 wt. % iron, 13-17 wt. % nickel, 6-8 wt. % molybdenum. Another type of cobalt-chromium alloy is L605 alloy that includes 18-22 wt. % chromium, 14-16 wt. % tungsten, 9-11 wt. % nickel, balance cobalt. As defined herein, a titanium-aluminum-vanadium alloy (TiAlV alloy) includes 5.5-6.75 wt. % aluminum, 3.5-4.5 wt. % vanadium, 85-93 wt. % titanium, 0-0.4 wt. % iron, 0-0.2 wt. % carbon. One type of titanium-aluminum-vanadium alloy is Ti-6Al-4V alloy that includes 3.5-4.5 wt. % vanadium, 5.5-6.75 wt. % aluminum, 0.3 wt. % max iron, 0.08 wt. % max carbon, 0.05 wt. % max yttrium, balance titanium. As defined herein, an aluminum alloy includes 80-99 wt. % aluminum, 0-12 wt. % silicon, 0-5 wt. % magnesium, 0-1 wt. % manganese, 0-0.5 wt. % scandium, 0-0.5 wt. % beryllium, 0-0.5 wt. % yttrium, 0-0.5 wt. % cerium, 0-0.5 wt. % chromium, 0-3 wt. % iron, 0-0.5, 0-9 wt. % zinc, 0-0.5 wt. % titanium, 0-3 wt. % lithium, 0-0.5 wt. % silver, 0-0.5 wt. % calcium, 0-0.5 wt. % zirconium, 0-1 wt. % lead, 0-0.5 wt. % cadmium, 0-0.05 wt. % bismuth, 0-1 wt. % nickel, 0-0.2 wt. % vanadium, 0-0.1 wt. % gallium, and 0-7 wt. % copper. As defined herein, a nickel alloy includes 30-98 wt. % nickel, 5-25 wt. % chromium, 0-65 wt. % iron, 0-30 wt. % molybdenum, 0-32 wt. % copper, 0-32 wt. % cobalt, 2-2 wt. % aluminum, 0-6 wt. % tantalum, 0-15 wt. % tungsten, 0-5 wt. % titanium, 0-6 wt. % niobium, 0-3 wt. % silicon. As defined herein, a titanium alloy includes 80-99 wt. % titanium, 0-6 wt. % aluminum, 0-3 wt. % tin, 0-1 wt. % palladium, 0-8 wt. % vanadium, 0-15 wt. % molybdenum, 0-1 wt. % nickel, 0-0.3 wt. % ruthenium, 0-6 wt. % chromium, 0-4 wt. % zirconium, 0-4 wt. % niobium, 0-1 wt. % silicon, 0.0.5 wt. % cobalt, 0-2 wt. % iron. As defined herein, a tungsten alloy includes 85-98 wt. % tungsten, 0-8 wt. % nickel, 0-5 wt. % copper, 0-5 wt. % molybdenum, 0-4 wt. % iron. As defined herein, a molybdenum alloy includes 90-99.5 wt. % molybdenum, 0-1 wt. % nickel, 0-1 wt. % titanium, 0-1 wt. % zirconium, 0-30 wt. % tungsten, 0-2 wt. % hafnium, 0-2 wt. % lanthanum. As defined herein, a copper alloy includes 55-95 wt. % copper, 0-40 wt. % zinc, 0-10 wt. % tin, 0-10 wt. % lead, 0-1 wt. % iron, 0-5 wt. % silicon, 0-12 wt. % manganese, 0-12 wt. % aluminum, 0-3 wt. % beryllium, 0-1 wt. % cobalt, 0-20 wt. % nickel. As defined herein, a beryllium-copper alloy includes 95-98.5 wt. % copper, 1-4 wt. % beryllium, 0-1 wt. % cobalt, and 0-0.5 wt. % silicon. As defined herein, a refractory metal alloy is a metal alloy that includes at least 20 wt. % of one or more of molybdenum, rhenium, niobium, tantalum or tungsten. Non-limiting refractory metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc. In one non-limiting embodiment, one or more or all of the components of the expandable interbody device is partially or fully formed of a metal alloy that includes at least 15 awt. % rhenium so as to improve the ductility and/or tensile strength of the metal alloy as compared to a metal alloy is that absent rhenium. Such improvement in ductility and/or tensile strength due to the inclusion of at least 15 awt. % rhenium in the metal alloy is referred to as the "rhenium effect." As defined herein, a "rhenium effect" is a) an increase of at least 10% in ductility of the metal alloy caused by the addition of rhenium to the metal alloy, and/or b) an increase of at least 10% in tensile strength of the metal alloy caused by the addition of rhenium to the metal alloy. In another non-limiting embodiment, the first and/or second endplates of the expandable interbody device are partially or fully formed of titanium alloy, molybdenum alloy rhenium alloy, or metal alloy that includes at least 5 awt. % rhenium. In another non-limiting embodiment, the drive block, pins, linkage block, drive screw, and/or linkages are partially or fully formed of titanium alloy, molybdenum alloy rhenium alloy, or metal alloy that includes at least 5 awt. % rhenium. The material used to form the different components of the expandable interbody device can be the same or different.

In another and/or alternative non-limiting aspect of the disclosure, one or more portions of the outer surface of the expandable interbody device can be coated with an enhancement layer. Non-limiting enhancement layers include chromium nitride (CrN), diamond-like carbon (DLC), titanium nitride (TiN), titanium oxynitride or titanium nitride oxide ($TiNO_x$), zirconium nitride (ZrN), zirconium oxide ($ZrO_2$), zirconium oxynitride ($ZrN_xO_y$) [e.g., cubic ZrN:O, cubic $ZrO_2$:N, tetragonal $ZrO_2$:N, and monoclinic $ZrO_2$:N phase coatings], oxyzirconium-nitrogen-carbon (ZrNC), zirconium OxyCarbide (ZrOC), and combinations of such coatings. In one non-limiting embodiment, the one or more enhancement layers are optionally applied to a portion or all of the outer surface of the expandable interbody device by use of a physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process. In another non-limiting embodiment, the thickness of the enhancement layer is greater than 1 nanometer (e.g., 2 nanometers to 100 microns and all values and ranges therebetween), and typically 0.1-25 microns, and more typically 0.2-10 microns. In another non-limiting embodiment, the hardness of the enhancement layer can be at least 5 GPa (ASTM C1327-15 or ASTM C1624-05), typically 5-50 GPa (and all values and ranges therebetween), more typically 10-25 GPa, and still more typically 14-24 GPa. In another non-limiting embodiment, the coefficient of friction (COF) of the enhancement layer can be 0.04-0.2 (and all values and ranges therebetween), and typically 0.6-0.15. In another non-limiting embodiment, the wear rate of the enhancement layer can be $0.5 \times 10^{-7}$ mm$^3$/N-m to $3 \times 10^{-7}$ mm$^3$/N-m (an all values and ranges therebetween), and typically $1.2 \times 10^{-7}$ mm$^3$/N-m to $2 \times 10^{-7}$ mm$^3$/N-m. In another non-limiting embodiment, the enhancement layer includes no more than 0.1 wt. % nickel, no more than 0.1 wt. % chromium, and/or no more than 0.1 wt. % cobalt. In another non-limiting embodiment, the outer surface of the metal portion of the expandable interbody device includes no more than 0.1 wt.

% nickel, no more than 0.1 wt. % chromium, and/or no more than 0.1 wt. % cobalt. The adhesion layer, when used to facilitate in adhering the enhancement layer to the expandable interbody device, includes no more than 0.1 wt. % nickel, no more than 0.1 wt. % chromium, and/or no more than 0.1 wt. % cobalt. In accordance with another non-limiting embodiment, the chromium nitride (CrN) coating generally includes 40-85 wt. % Cr (and all values and ranges therebetween), 15-60 wt. % N (and all values and ranges therebetween), 0-10 wt. % Re (and all values and ranges therebetween), 0-10 wt. % Si (and all values and ranges therebetween), 0-2 wt. % O (and all values and ranges therebetween), and 0-2 wt. % C (and all values and ranges therebetween). In another non-limiting embodiment, the diamond-Like Carbon (DLC) coating generally includes 60-99.99 wt. % C (and all values and ranges therebetween), 0-2 wt. % N (and all values and ranges therebetween), 0-10 wt. % Re (and all values and ranges therebetween), 0-20 wt. % Si (and all values and ranges therebetween), and 0-2 wt. % O (and all values and ranges therebetween). In another non-limiting embodiment, the ratio of N to O when forming the $TiNO_x$ coating is generally 1:10 to 10:1 (and all values and ranges therebetween). In another non-limiting embodiment, the enhancement layer composition generally includes 20-85 wt. % Ti (and all values and ranges therebetween), 0.5-35 wt. % N (and all values and ranges therebetween), 0-10 wt. % Re (and all values and ranges therebetween), and 0.5-35 wt. % O (and all values and ranges therebetween). In another non-limiting embodiment, the enhancement layer composition generally includes 35-90 wt. % Zr (and all values and ranges therebetween), 5-25 wt. % N (and all values and ranges therebetween), 0-10 wt. % Re (and all values and ranges therebetween), 0-20 wt. % Si (and all values and ranges therebetween), 0-2 wt. % O (and all values and ranges therebetween), and 0-2 wt. % C (and all values and ranges therebetween). In another non-limiting embodiment, the enhancement layer composition generally includes 35-90 wt. % Zr (and all values and ranges therebetween), 10-35 wt. % O (and all values and ranges therebetween), 0-2 wt. % N (and all values and ranges therebetween), 0-10 wt. % Re (and all values and ranges therebetween), 0-20 wt. % Si (and all values and ranges therebetween), and 0-2 wt. % C (and all values and ranges therebetween). In another non-limiting embodiment, the enhancement layer composition generally includes 40-95 wt. % Zr (and all values and ranges therebetween), 5-25 wt. % O (and all values and ranges therebetween), and 10-40 wt. % C (and all values and ranges therebetween), 0-2 wt. % N (and all values and ranges therebetween), 0-10 wt. % Re (and all values and ranges therebetween), and 0-20 wt. % Si (and all values and ranges therebetween). In another non-limiting embodiment, the enhancement layer composition generally includes 20-85 wt. % Zr (and all values and ranges therebetween), 0.5-35 wt. % N (and all values and ranges therebetween), and 0.5-35 wt. % O (and all values and ranges therebetween). In another non-limiting embodiment, the enhancement layer composition generally includes 40-95 wt. % Zr (and all values and ranges therebetween), 5-40 wt. % N (and all values and ranges therebetween), and 5-40 wt. % C (and all values and ranges therebetween), 0-2 wt. % O (and all values and ranges therebetween), 0-10 wt. % Re (and all values and ranges therebetween), and 0-20 wt. % Si (and all values and ranges therebetween).

In accordance with another and/or alternative non-limiting aspect of the present disclosure, the expandable interbody device can optionally be partially (e.g., 1% to 99.99% and all values and ranges therebetween) or fully be coated with and/or include one or more agents. When one or more agents are coated on the expandable interbody device, and the expandable interbody device includes an enhancement layer, one or more agents are generally coated on the outer surface of the enhancement layer. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. The term "agent" does not include a material used to form an enhancement layer. Non-limiting examples of clinical events that can be addressed by one or more agents include, but are not limited to, viral, fungus and/or bacterial infection; vascular diseases and/or disorders; lymphatic diseases and/or disorders; cancer; implant rejection; pain; nausea; swelling; organ failure; immunity diseases and/or disorders; cell growth inhibitors, blood diseases and/or disorders; heart diseases and/or disorders; neuralgia diseases and/or disorders; fatigue; genetic diseases and/or disorders; trauma; cramps; muscle spasms; tissue repair; nerve repair; neural regeneration and/or the like. The type and/or amount of agent included coated on the expandable interbody device can vary. In accordance with another and/or alternative aspect of the present disclosure, one or more portions of the frame for a prosthetic heart valve can optionally 1) include the same or different agents, 2) include the same or different amount of one or more agents, 3) include the same or different polymer coatings, 4) include the same or different coating thicknesses of one or more polymer coatings, 5) have one or more portions of the expandable interbody device controllably release and/or uncontrollably release one or more agents, and/or 6) have one or more portions of the expandable interbody device controllably release one or more agents and one or more portions of the expandable interbody device uncontrollably release one or more agents.

In accordance with another and/or alternative aspect of the present disclosure, one or more surfaces of the expandable interbody device can optionally be treated to achieve the desired coating properties of the one or more agents and/or one or more polymers coated on the expandable interbody device. Such surface treatment techniques include, but are not limited to, cleaning, buffing, smoothing, nitriding, annealing, swaging, cold working, etching (chemical etching, plasma etching, etc.), etc. As can be appreciated, other or additional surface treatment processes can be used prior to the coating of one or more agents and/or polymers on the surface of the expandable interbody device.

In another and/or alternative non-limiting aspect of the disclosure, one or more portions of the expandable interbody device can optionally include a marker material that facilitates enabling the expandable interbody device to be properly positioned in the treatment area. The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, infrared waves, ultraviolet waves, etc.).

In one non-limiting object of the disclosure, there is provided an expandable interbody device that can be used as a prosthesis used during spinal surgery.

In another and/or alternative non-limiting object of the disclosure, there is provided an expandable interbody device that is configured to be inserted into the space between spinal disks to provide stability.

In another and/or alternative non-limiting object of the disclosure, there is provided an expandable interbody device that is configured to be inserted between vertebrae of a patient's spine (e.g., in the disk space between adjacent vertebrae) for fixation with bone to immobilize the joint as part of a surgical treatment.

In another and/or alternative non-limiting object of the disclosure, there is provided an expandable interbody device that includes a drive block, a linkage block, a drive screw, a first endplate, a second endplate, and a first set of linkages that includes first and second linkages, and wherein a) the drive block optionally at least partially forms or includes a drive block opening, and the linkage block optionally at least partially forms or includes a linkage block opening, and b) the drive screw is rotatably coupled at least partially in the drive block opening or linkage block opening and is threadingly disposed within the other of the linkage block opening or the drive block opening.

In another and/or alternative non-limiting object of the disclosure, there is provided an expandable interbody device that includes a drive block, a linkage block, a drive screw, a first endplate, a second endplate, and a first set of linkages that includes first and second linkages, and wherein a) the drive block includes a drive block opening and a head of the drive screw is rotatably coupled in a portion of the drive block opening, b) the head of the drive screw that is located in the drive block opening is not threadedly coupled to the drive block, c) during rotation of the drive screw, the head of the drive screw is able to rotate within the drive block opening, but does move or moves less than 5% the longitudinal length of the drive block opening, d) the linkage block includes a linkage block opening and at least a portion of the linkage block opening includes threading, e) the body of the drive screw includes threading that is threadedly connected to at least a portion of the threading in the linkage block opening, f) during rotation of the drive screw a portion of the body of the drive screw moves with the linkable block opening along a longitudinal axis of the linkage block opening, and g) during rotation of the drive screw a distance between the drive block opening and the linkage block opening is caused to change.

In another and/or alternative non-limiting object of the disclosure, there is provided an expandable interbody device that includes a drive block, a linkage block, a drive screw, a first endplate, a second endplate, and a first set of linkages that includes first and second linkages, and wherein a) the drive block includes a drive block opening and at least a portion of the drive block opening includes threading, b) a head of the drive screw is threadedly coupled to a portion of the threading in the drive block opening, c) during rotation of the drive screw, the head of the drive screw is able to rotate within the drive block opening, and moves with the drive block opening along a longitudinal axis of the drive block opening, d) the linkage block includes a linkage block opening, e) the body of the drive screw is rotatably connected to at least a portion of the linkage block opening, f) during rotation of the drive screw, a portion of the body of the drive screw is able to rotate within the linkage block opening, but does move or moves less than 5% the longitudinal length of the linkage block opening, and g) during rotation of the drive screw a distance between the drive block opening and the linkage block opening is caused to change.

In another and/or alternative non-limiting object of the disclosure, there is provided an expandable interbody device that includes a drive block, and a drive screw and wherein the drive block opening of the drive block is configured such that the proximal end of the head of the drive screw that is located farthest from the body of the drive screw always remains within the drive block opening of the drive block during the full expansion and fully contraction of the expandable interbody device.

In another and/or alternative non-limiting object of the disclosure, there is provided an expandable interbody device that includes a drive block, and a drive screw and wherein a) the head of the screw includes a rib about a portion of all of the outer circumference of the head and the rib is position in a slot in a portion or all of an inner circumference of the drive block opening so that the head of the drive screw can rotate in drive block open, but not move along the longitudinal length of the drive block opening during the rotation of the drive screw, and/or b) the head of the screw includes a slot about a portion of all of the outer circumference of the head and the slot is position in a rib in a portion or all of an inner circumference of the drive block opening so that the head of the drive screw can rotate in drive block open, but not move along the longitudinal length of the drive block opening during the rotation of the drive screw.

In another and/or alternative non-limiting object of the disclosure, a first end portion of the first linkage on the first set of linkages is rotatably coupled the linkage block and the second end portion of the first linkage on the first set of linkages engages the first endplate, and a first end portion of the second linkage on the first set of linkages is rotatably coupled the linkage block and the second end portion of the second linkage on the first set of linkages engages the second endplate.

In another and/or alternative non-limiting object of the disclosure, rotation of the drive screw causes movement of the linkage block relative to the drive block and movement of the first endplate relative to the second endplate.

In another and/or alternative non-limiting object of the disclosure, the second end portion of the first linkage on the first set of linkages includes a first linkage pin that is used to a) facilitate in the movement of the first endplate when the drive screw is rotated to cause a distance between the drive block opening and the linkage block opening is caused to change, b) facilitates in maintaining the engagement of the second end portion of the first linkage and/or the first linkage pin to the first endplate during movement of the first endplate when the drive screw is rotated to cause a distance between the drive block opening and the linkage block opening is caused to change, c) rotatably engage the second end portion of the first linkage on the first set of linkages to the first endplate, but not rotatably secured and/or attached to the first endplate, and/or d) rotatably attach the second end portion of the first linkage on the first set of linkages to the first endplate.

In another and/or alternative non-limiting object of the disclosure, the second end portion of the second linkage on the first set of linkages includes a second linkage pin that is used to a) facilitate in the movement of the second endplate when the drive screw is rotated to cause a distance between the drive block opening and the linkage block opening is caused to change, b) facilitates in maintaining the engagement of the second end portion of the second linkage and/or the second linkage pin to the second endplate during movement of the second endplate when the drive screw is rotated to cause a distance between the drive block opening and the linkage block opening is caused to change, c) rotatably engage the second end portion of the second linkage on the first set of linkages to the second endplate, but not rotatably secured and/or attached to the second endplate, and/or d)

rotatably attach the second end portion of the second linkage on the first set of linkages to the second endplate.

In another and/or alternative non-limiting object of the disclosure, the expandable interbody device further includes a second set of linkages that includes first and second linkages, and wherein the second set of linkages are positioned on the opposite side of the expandable interbody device from the expandable interbody device, and the first end portion of the first linkage on the second set of linkages is rotatably coupled the linkage block and the second end portion of the first linkage on the second set of linkages engages the first endplate, and a first end portion of the second linkage on the second set of linkages is rotatably coupled the linkage block and the second end portion of the second linkage on the second set of linkages engages the second endplate.

In another and/or alternative non-limiting object of the disclosure, the first portion of the first and second linkages of the first and/or second set of linkages are rotatably coupled to the linkage block along the same rotation axis.

In another and/or alternative non-limiting object of the disclosure, both the linkage housing and the linkage bar include a screw opening and when the linkage bar is positioned in the linkage housing, and wherein the screw openings of the linkage bar and the linkage housing are configured to align such that at least a portion of the drive screw body is positioned through both of the screw openings of the linkage bar and the linkage housing.

In another and/or alternative non-limiting object of the disclosure, the drive block and the first and/or second endplates include one or more engagement members (e.g., slot, protrusion, rib, rail, groove, etc.) that are configured to slidably engage with respect to one another so as to facilitate in a) guiding of movement of the first and/or second endplates relative to the drive block as the expandable interbody device moves from the fully closed or collapsed position to the fully open or expanded position, and/or b) inhibiting or prevent over expansion of the first and/or second endplates relative to the drive block as the expandable interbody device moves from the fully closed or collapsed position to the fully open or expanded position.

In another and/or alternative non-limiting object of the disclosure, the drive block includes one or more guide flanges on one or both sides of the drive block, and the first and/or second endplates include one or more guide slots on one or both sides of the first and/or second endplates, and where the guide slot is configured to slidably receive at least a portion of a guide flange.

In another and/or alternative non-limiting object of the disclosure, the drive block and the linkage block move along a longitudinal axis of the first and/or second endplates as the expandable interbody device moves from the fully closed or collapsed position to the fully open or expanded position.

In another and/or alternative non-limiting object of the disclosure, both the proximal and distal ends of the first and second endplates move away from one another as the expandable interbody device moves from the fully closed or collapsed position to the fully open or expanded position.

In another and/or alternative non-limiting object of the disclosure, the first and second endplates include an opening through the top and bottom surfaces of the first and second endplates, and the drive block includes an opening through the top and bottom surfaces of the drive block, and the openings in the first and second endplates and the opening in the drive block are at least partially aligned with one another as the expandable interbody device is in the fully closed or collapsed position and the fully open or expanded position, and also when the expandable interbody device moves from the fully closed or collapsed position to the fully open or expanded position.

In another and/or alternative non-limiting object of the disclosure, the proximal end of the drive block includes one or more pin slots, and the proximal end of the first and/or second endplates includes a plate slot, and wherein the pin slot and the plate slot are configured to receive a guide pin that is configured to limit the amount of movement of the proximal end of the drive block relative to the first and/or second endplates as the expandable interbody device moves from the fully closed or collapsed position to the fully open or expanded position.

In another and/or alternative non-limiting object of the disclosure, the expandable interbody device optionally includes one or more graft windows, cavities and/or slots.

In another and/or alternative non-limiting object of the disclosure, the expandable interbody device optionally includes first and/or second endplates that include a micro-textured surface and/or one or more teeth.

In another and/or alternative non-limiting object of the disclosure, the expandable interbody device optionally includes first and second endplates that include planar top surfaces that do not lie within the same plane when the expandable interbody device is in the fully expanded position.

In another and/or alternative non-limiting object of the disclosure, the expandable interbody device optionally includes first and second endplates that include planar top surfaces that lie within or closely within the same plane when the expandable interbody device is in the fully contracted position.

In another and/or alternative non-limiting object of the disclosure, one or more or all of the components of the expandable interbody device is partially or fully formed of a metal alloy selected from a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) refractory metal alloy, or l) metal alloy that includes at least 5 awt. % rhenium.

In another and/or alternative non-limiting object of the disclosure, one or more portions of the outer surface of the expandable interbody device are coated with an enhancement layers such as chromium nitride (CrN), diamond-like carbon (DLC), titanium nitride (TiN), titanium oxynitride or titanium nitride oxide ($TiNO_x$), zirconium nitride (ZrN), zirconium oxide ($ZrO_2$), zirconium oxynitride ($ZrN_xO_y$) [e.g., cubic ZrN:O, cubic $ZrO_2$:N, tetragonal $ZrO_2$:N, and monoclinic $ZrO_2$:N phase coatings], oxyzirconium-nitrogen-carbon (ZrNC), zirconium OxyCarbide (ZrOC), and combinations of such coatings.

In another and/or alternative non-limiting object of the disclosure, the expandable interbody device can optionally be partially or fully be coated with and/or include one or more agents.

In another and/or alternative non-limiting object of the disclosure, one or more portions of the expandable interbody device can include a marker material that facilitates enabling the expandable interbody device to be properly positioned in the treatment area.

In another and/or alternative non-limiting object of the disclosure, the angle formed by the plane of 50-100% of the top surface of the first and second endplates is about 15°-50° when the expandable interbody device is in the fully expanded position.

In another and/or alternative non-limiting object of the disclosure, the angle formed by the plane of 50-100% of the top surface of the first and second endplates is about 20°-40° when the expandable interbody device is in the fully expanded position.

In another and/or alternative non-limiting object of the disclosure, the angle formed by the plane of 50-100% of the top surface of the first and second endplates is about 0°-5° when the expandable interbody device is in the fully contracted position.

In another and/or alternative non-limiting object of the disclosure, the angle formed by the plane of 50-100% of the top surface of the first and second endplates is about 5°-30° when the expandable interbody device is in the fully contracted position.

Other objects, advantages, and novel features of the present invention will become apparent from the following detailed description of the invention when considered in conjunction with the accompanying drawings.

BRIEF DESCRIPTION OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. Reference may now be made to the drawings, which illustrate various embodiments that the disclosure may take in physical form and in certain parts and arrangement of parts wherein.

DETAILED DESCRIPTION OF NON-LIMITING EMBODIMENTS

Figure 1:
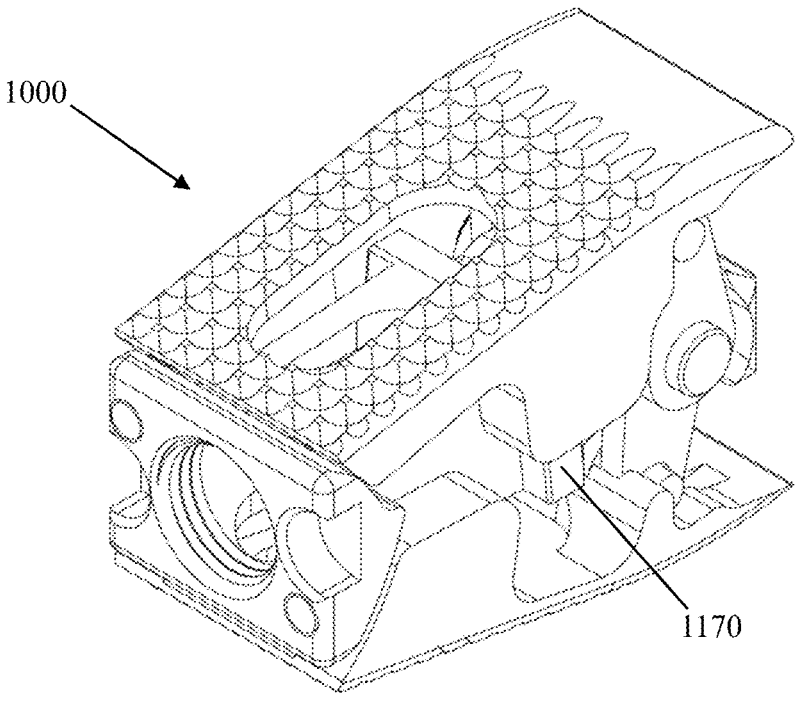
FIG. 1 is a top isometric view one non-limiting expandable prosthetic device in a fully open or expanded position in accordance with one non-limiting aspect of the present disclosure.

A more complete understanding of the articles/devices, processes and components disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g., "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

For the sake of simplicity, the attached figures may not show the various ways (readily discernable, based on this disclosure, by one of ordinary skill in the art) in which the disclosed system, method and apparatus can be used in combination with other systems, methods and apparatuses. Additionally, the description sometimes uses terms such as "produce" and "provide" to describe the disclosed method. These terms are abstractions of the actual operations that can be performed. The actual operations that correspond to these terms can vary depending on the particular implementation and are, based on this disclosure, readily discernible by one of ordinary skill in the art.

Referring now to the drawings wherein the showings are for the purpose of illustrating non-limiting embodiments of the disclosure only and not for the purpose of limiting same, FIG. 1-14 illustrate devices, systems, and methods for an expandable prosthetic device 1000. The expandable prosthetic device 1000 includes linkages that allow for movement of the endplates relative to each other, and curved ramps that allow for simultaneous movement of the first and second endplates relative to each other along specific paths to achieve a desired height and lordosis of the expandable prosthetic device 1000 when expanded from the fully closed or collapsed position to the fully open or expanded position. The expandable prosthetic device 1000 includes a drive block, a set of ramps, a linkage block, a drive screw, a first endplate, a second endplate, and at least two linkages. The drive block defines a drive block opening, and the linkage block defines a linkage block opening. The drive screw is rotatably coupled within one of the drive block opening or linkage block opening and is threadingly disposed within the other of the linkage block opening or the drive block opening. The first endplate includes a ramp slot that slidingly engages with one of the ramps on the drive block, and the second endplate includes a ramp slot that slidingly engages with another of the ramps on the drive block. Rotation of the drive screw causes movement of the linkage block relative to the drive block and movement of the first endplate relative to the second endplate.

Figure 7:
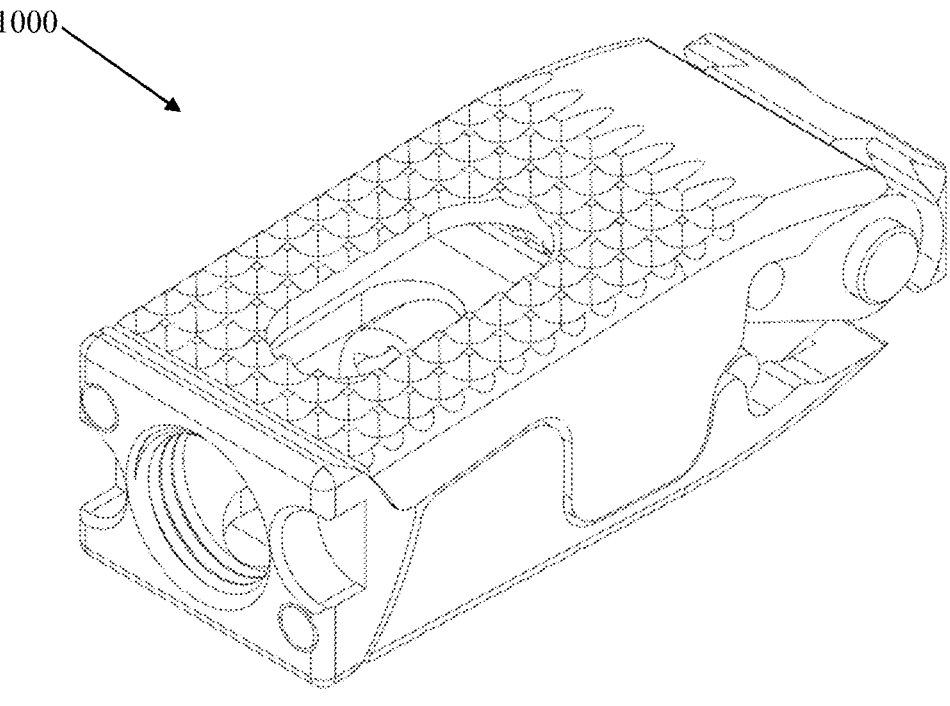
FIG. 7 is a top isometric view of the expandable prosthetic device of FIG. 1 in a closed or collapsed position.
Figure 8:
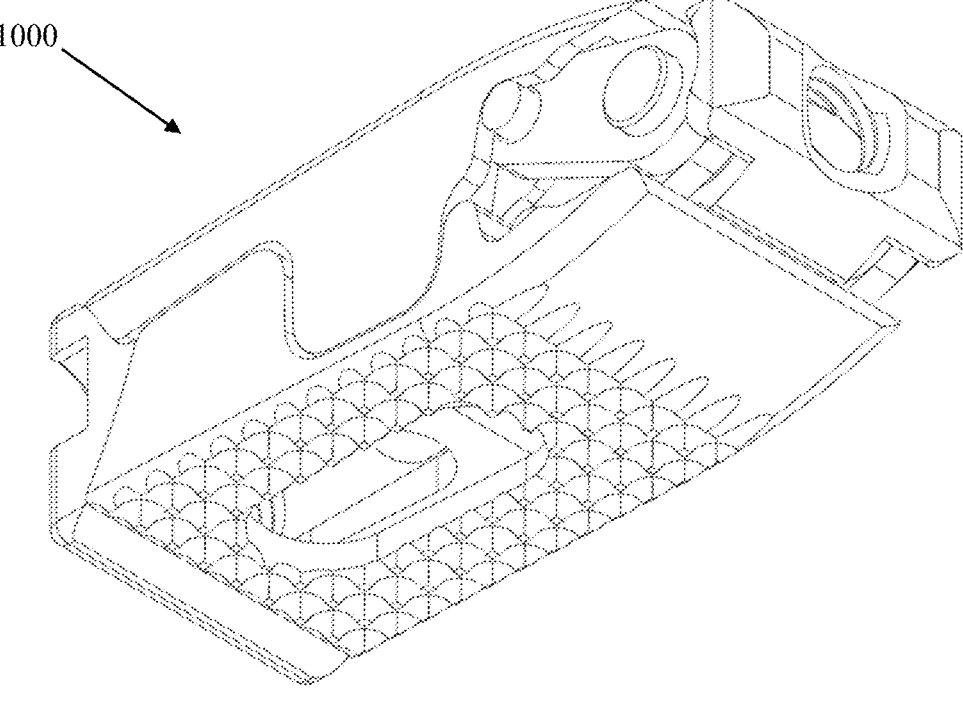
FIG. 8 is a bottom isometric view of the expandable prosthetic device of FIG. 7.

Referring now to FIGS. 1-14, one non-limiting expandable prosthetic device 1000 is illustrated. FIG. 1 illustrates the expandable prosthetic device 1000 in a fully expanded or open position and FIG. 7 illustrates the expandable prosthetic device 1000 is in the fully closed or collapsed position.

The expandable prosthetic device 1000 includes a drive block 1100, a linkage block 1200, a drive screw 1300, a first endplate 1400, a second endplate 1500, and includes one or both of first and second sets of linkages 1600, 1610, wherein the first set of linkage 1600 includes linkages 1600a, b, and the second set of linkage includes linkages 1610a, b.

The drive block 1100 includes a first or proximal side 1102, a second or distal side 1104 opposite and spaced apart from the first side 1102, a third side 1106 extending between the first side 1102 and the second side 1104, a fourth side 1108 opposite and spaced apart from the third side 1106. The first end 1102 of the drive block 1100 defines a drive block opening 1120. The drive block 1100 includes a slot region 1160 that is located between the first side 1102, the second side 1104, the third side 1106 and the fourth side 1108 of the drive block 1100. The slot region 1160 can optionally include a top opening on the top side of the drive block 1100 and/or a bottom opening on the bottom side of the drive block 1100.

The drive block 1100 also includes first and second block ramps 1170, 1180 that are positioned in the third side 1106 and fourth side 1108 respectively of the drive block 1100. The first and second block ramps 1170, 1180 are illustrated as having an arcuate profile; however, this is not required. The first and second block ramps 1170, 1180 can optionally be spaced the same distance from the distal end of the drive block 1100. The first and second block ramps 1170, 1180 are illustrated as having a length that is about 30-100% (and all values and ranges therebetween), and typically about 50-70% of the height of the distal end of the drive block; however, this is not required.

Figure 13:
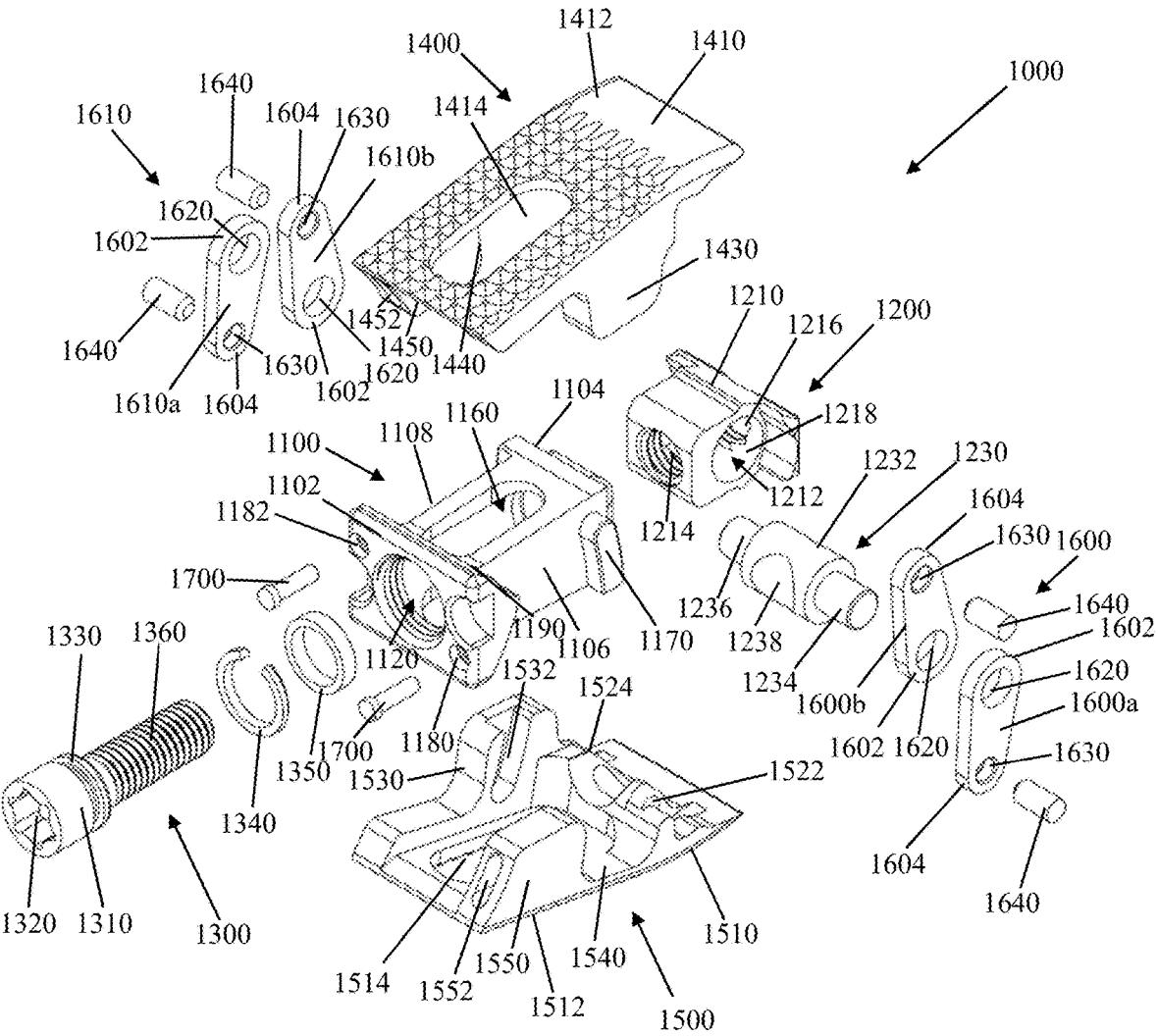
FIG. 13 is an exploded view of the expandable prosthetic device of FIG. 1.
Figure 14:
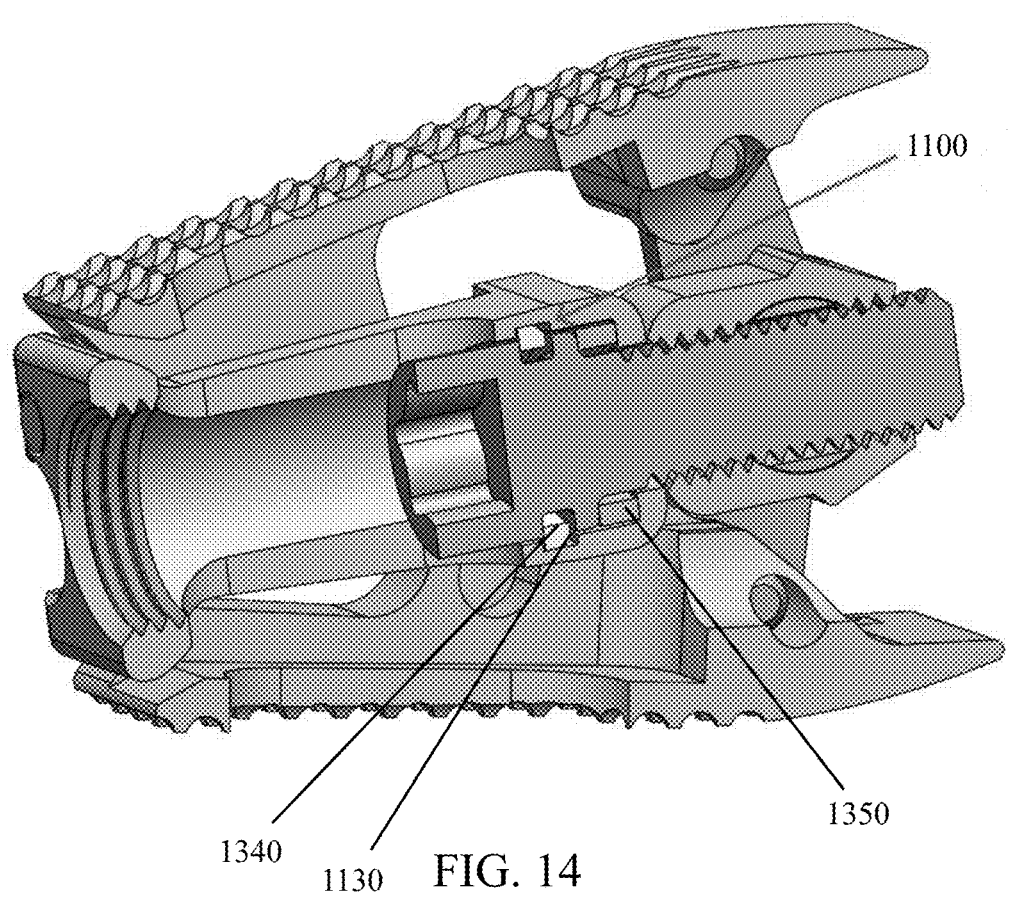
FIG. 14 is a cross-sectional view along the central longitudinal axis of the expandable prosthetic device of FIG. 1.

The drive block opening 1120 has a slot 1130 adjacent the front end of the first side 1102. The drive block opening 1120 may or may not include threading. The optional threading, when threading is used, can be used to threadedly engage an insertion tool (not shown). The insertion tool can be releasable connected to the expandable prosthetic device 1000 via the threading. The insertion tool can be used to insert the expandable prosthetic device 1000 into a treatment area (e.g., between bones in foot, between bones in an ankle, between bones in the hand, between bones in the wrist, between bones in the spine, etc.). The insertion, when at least partially positioned in the drive block opening 1120 can optionally be configured to rotate the drive screw 1300 to cause the expandable prosthetic device 1000 to move between the fully closed or collapsed position and the fully open or expanded position, as will be discussed in more detail below. As illustrated in FIG. 13, the head 1310 of the drive screw 1300 can optionally include a screw opening 1320 that allows an insertion tool to releasably engage the head 1310 of the drive screw 1300 so as to facilitate in the rotation of the drive screw 1300 by the insertion tool. The shape of the screw opening 1320 is non-limiting (e.g., star-shaped, polygonal shaped, oval shaped, etc.).

The head 1310 of the drive screw 1300 can include a securing arrangement such as a slot 1330, rib, or some other arrangement that is used to facilitate in rotatable securing the head 1310 of the drive screw 1300 in the drive block opening 1120. In one non-limiting arrangement, a lock ring 1340 is at least partially inserted in a slot 1330 in the head 1310 of the drive screw 1300 and slot 1130 in the drive block opening 1120 to facilitate in rotatable securing the head 1310 of the drive screw 1300 in the drive block opening 1120.

When the head 1310 of the drive screw 1300 is rotatably positioned and secured in the drive block opening 1120, the end of the head 1310 of the drive screw 1300 can be configured such that it does not extend outwardly from the drive block opening 1120. In one non-limiting arrangement, when the head 1310 of the drive screw 1300 is rotatably positioned and secured in the drive block opening 1120, the end of the head 1310 of the drive screw 1300 is recessed in the drive block opening 1120.

A bushing 1350 can optionally be used with the drive screw 1300 and be partially or fully positioned in the drive block opening 1120. The bushing 1350, when used, facilitates in the rotation of the head 1310 of the drive screw 1300 in the drive block opening 1120.

As illustrated in FIG. 13, the drive screw 1300 includes a body portion 1360 that includes threading. The body portion 1360 can have a diameter that is less than the head 1310 of the drive screw 1300. As will be discussed in more detail below, the threading on the body portion 1360 threadedly engages the linkage block 1200 and causes the linkage block 1200 to move relative to the drive block 1100 when the drive screw 1300 is rotated. When the expandable prosthetic device 1000 is fully assembled, all or a portion of the body portion 1360 extends into and through the slot region 1160 of the drive block 1100. The head 1310 of the drive screw 1300 can be configured such that the head 1310 cannot full pass through the drive block opening 1120.

The linkage block 1200 includes a linkage housing 1210 and a linkage bar 1230. The linkage housing 1210 includes a housing cavity 1212, a front opening 1214, a rear opening 1216, a first side opening 1218 and a second side opening 1220. The housing cavity 1212 opens to the front opening 1214, the rear opening 1216, the first side opening 1218 and the second side opening 1220. The linkage housing 1210 is configured to be position rearwardly of the drive block 1100 and be moveable relative to drive block 1100 along the longitudinal axis of the expandable prosthetic device 1000 when the expandable prosthetic device 1000 is fully assembled.

The linkage bar 1230 includes a linkable body 1232 and a first flange 1234 positioned at one end of the linkage body 1230 and a second flange 1236 positioned at the opposite end of the linkage body 1232. A linkage opening 1238 is located in the linkage body 1232. The linkage body 1230 is configured to be inserted through a first side opening 1218 and a second side opening 1220 of the linkage housing 1210 such that a) the first flange 1234 extends outwardly from the first side opening 1218 when the linkage bar 1230 is positioned in the linkage housing 1210, b) the second flange 1236 extends outwardly from the second side opening 1220 when the linkage bar 1230 is positioned in the linkage housing 1210, and c) the linkage opening 1238 is partially or fully aligned with the front opening 1214 and the rear opening 1216 when the linkage bar 1230 is positioned in the linkage housing 1210. The partial or full alignment of the linkage opening 1238 with the front opening 1214 and the rear opening 1216 when the linkage bar 1230 is positioned in the linkage housing 1210 allows a portion of the body portion 1360 of the drive screw 1300 to pass through the linkage opening 1238, the front opening 1214 and the rear opening 1216 when the expandable prosthetic device 1000 is fully assembled. The linkage opening 1238, the front opening 1214 and/or the rear opening 1216 can optionally include threading that is configured to engage threading on the body portion 1360 of the drive screw 1300. As illustrated in FIG. 13, the front opening 1214 and/or the rear opening 1216 include threading that is configured to engage threading on the body portion 1360 of the drive screw 1300, and the linkage opening 1238 is absent threading.

Each of the first endplate 1400 and the second endplate 1500 include a body 1410, 1510. The body 1410, 1510 has a top side 1412, 1512 and a bottom side opposite and spaced apart from the top side 1412, 1512.

The top sides 1412, 1512 of the first and second endplates 1400, 1500 can optionally include a graft window 1414, 1514. The graft windows can optionally be used to facilitate bone growth once the expandable prosthetic device is inserted in a patient.

The top sides 1412, 1512 of the first and/or second endplates 1400, 1500 can optionally include a micro-textured surface and/or one or more teeth to create friction between the bone and the endplates. However, in other implementations, the first sides 1412, 1512 of the first and/or second endplates 1400, 1500 can include any number of teeth, no teeth, and/or no micro-textured surface.

Figure 9:
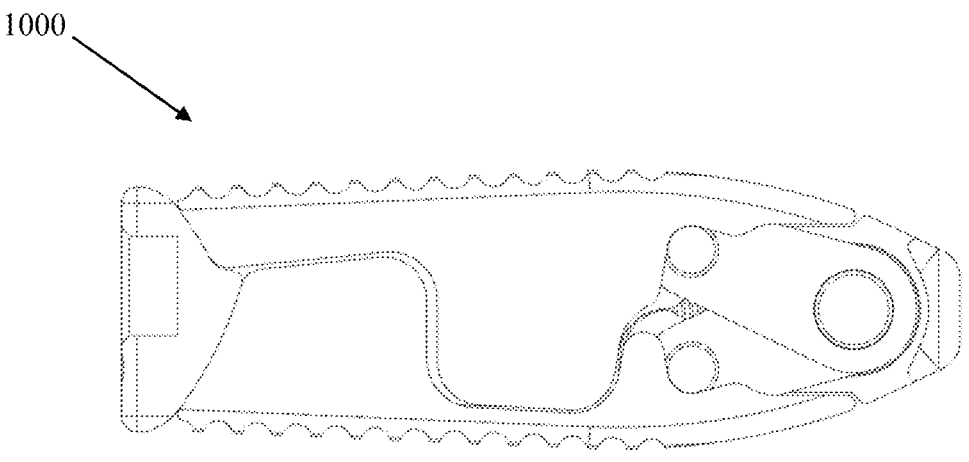
FIG. 9 is a side view of the expandable prosthetic device of FIG. 7.
Figure 10:
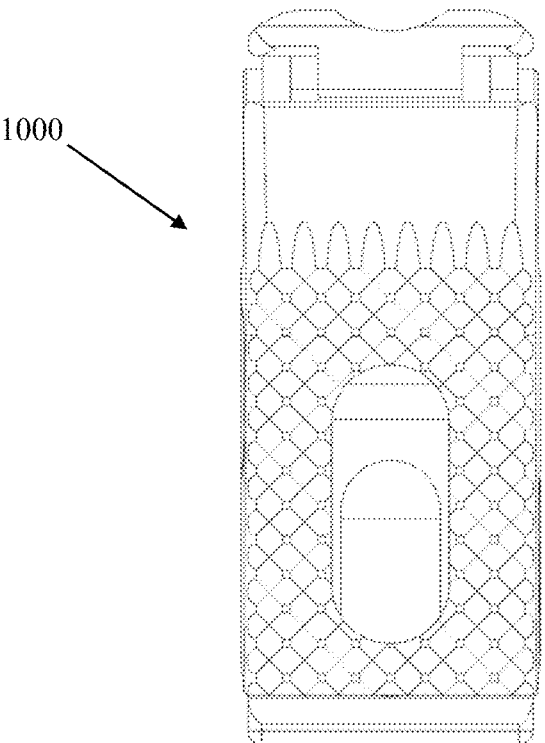
FIG. 10 is a top view of the expandable prosthetic device of FIG. 7.
Figure 11:
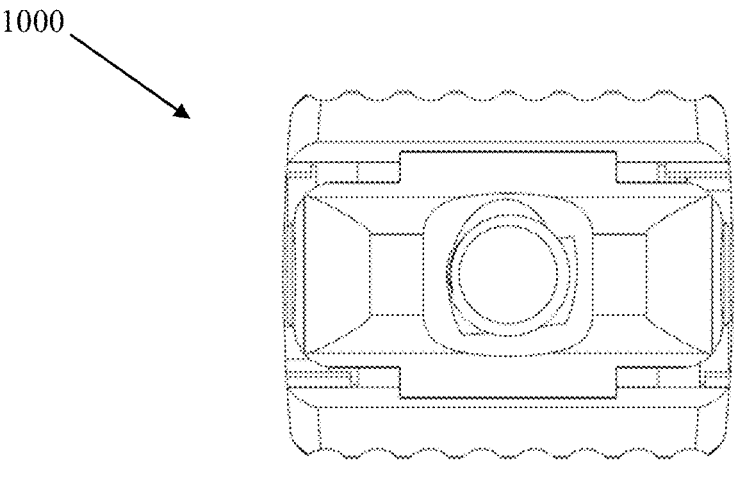
FIG. 11 is a distal end view of the expandable prosthetic device of FIG. 7.
Figure 12:
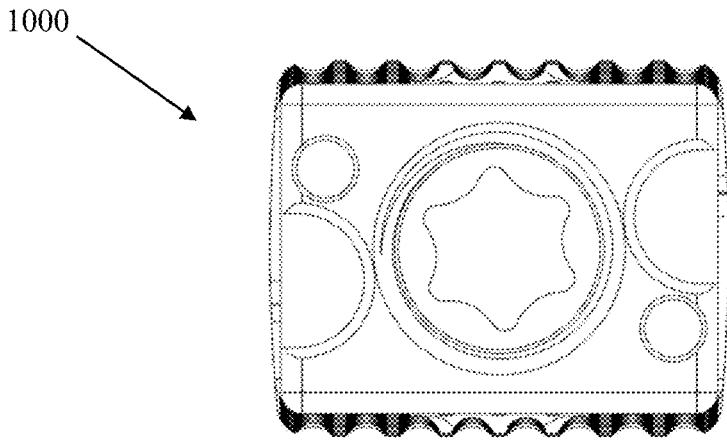
FIG. 12 is a proximal end view of the expandable prosthetic device of FIG. 7.

The first and second endplates 1400, 1500 can optionally include planar top surfaces that do not lie within the same plane. As best illustrated in FIGS. 9 and 13, the first and second endplates 1400, 1500 both include a front portion and a rear portion when the top surface of these two portions do not lie in the same plane. The rear portion of the first endplate 1400 slopes downwardly from the front portion at an angle of about 5-60° (and all values and ranges therebetween). The top surface of the front portion of the first endplate 1400 has a generally planar or flat surface along 50-100% (and all values and ranges therebetween) of the longitudinal length of the front portion. The longitudinal length of the rear portion is generally less than the longitudinal length of the front portion. Generally, the longitudinal length of the rear portion is 20-80% (and all values and ranges therebetween) of the longitudinal length of the front portion. As also illustrated in FIGS. 9 and 13, the rear portion of the second endplate 1500 slopes downwardly from the front portion at an angle of about 5-60° (and all values and ranges therebetween). The top surface of the front portion of the second endplate 1500 has a generally planar or flat surface along 50-100% (and all values and ranges therebetween) of the longitudinal length of the front portion. The longitudinal length of the rear portion is generally less than the longitudinal length of the front portion. Generally, the longitudinal length of the rear portion is 20-80% (and all values and ranges therebetween) of the longitudinal length of the front portion.

Figure 3:
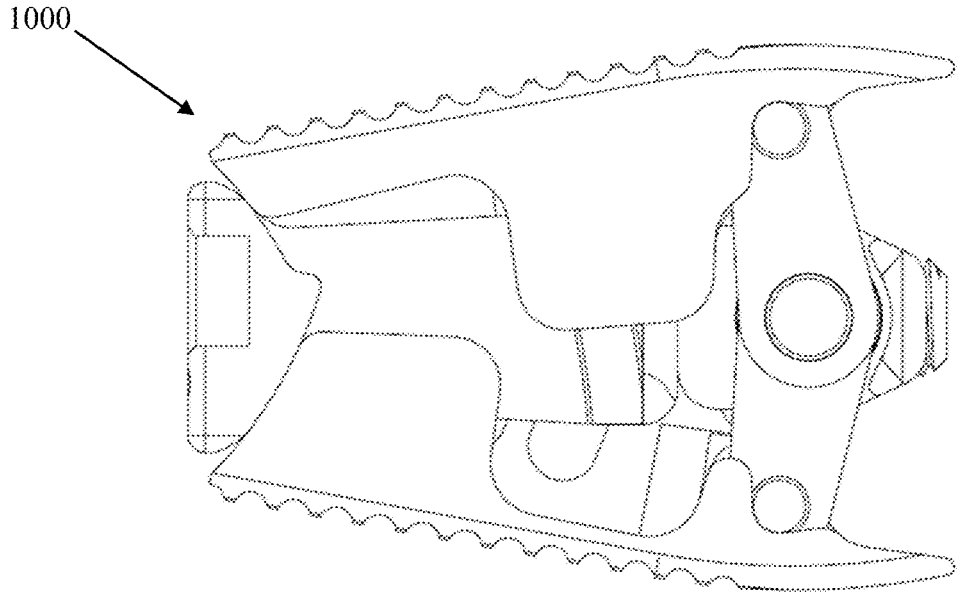
FIG. 3 is a side view of the expandable prosthetic device of FIG. 1.
Figure 4:
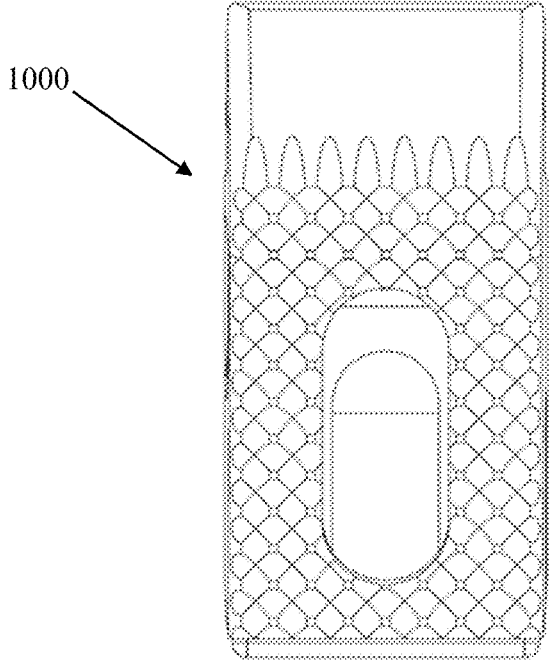
FIG. 4 is a top view of the expandable prosthetic device of FIG. 1.
Figure 5:
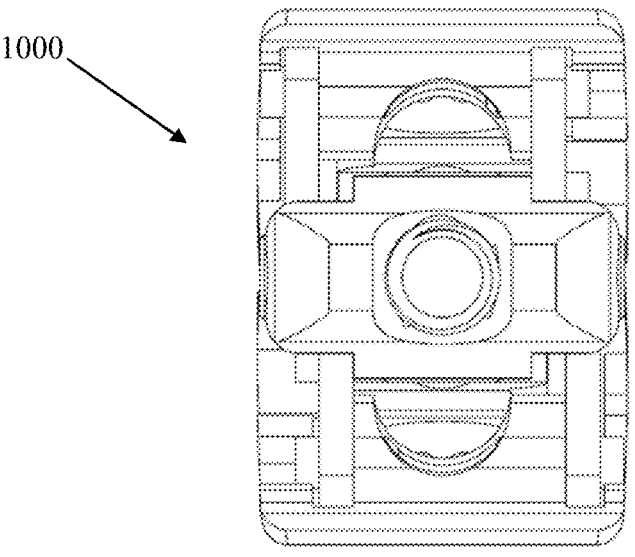
FIG. 5 is a distal end view of the expandable prosthetic device of FIG. 1.
Figure 6:
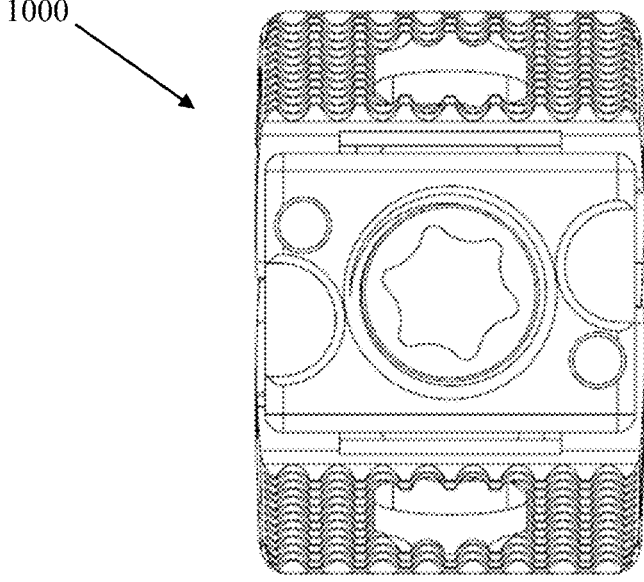
FIG. 6 is a proximal end view of the expandable prosthetic device of FIG. 1.

As illustrated in FIG. 9, the plane of the top surface of the front portion of the first endplate 1400 is generally parallel or slightly angled (e.g., ±10° and all values and ranges therebetween) to the plane of the of the top surface of the front portion of the second endplate 1500 when the expandable prosthetic device 1000 is in the fully closed or collapsed position. As illustrated in FIGS. 3 and 9, the front ends of the first and second endplates 1400, 1500 can be configured to not contact one another as the expandable prosthetic device 1000 moves from the fully closed or collapsed position to the fully open or expanded position.

The expandable prosthetic device 1000 includes first and second sets of linkages 1600, 1610, wherein the first set of linkage 1600 includes linkages 1600*a, b*, and the second set of linkage includes linkages 1610*a, b*. Each of the four linkages 1600*a*, 1600*b*, 1600*c*, 1600*d* has a longitudinal axis, a first portion 1602, and a second portion 1604 spaced apart from the first portion 1602 along the longitudinal axis.

Figure 2:
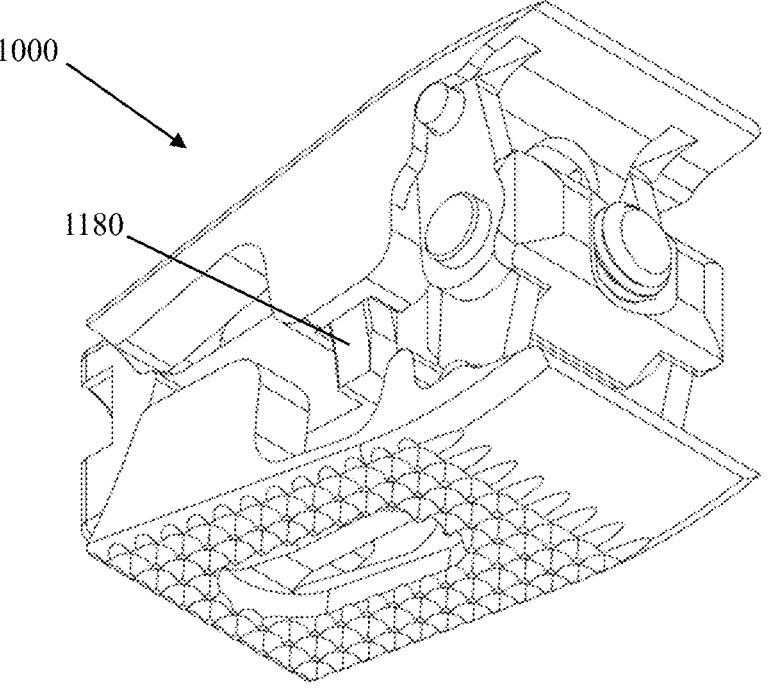
FIG. 2 is a bottom isometric view of the expandable prosthetic device of FIG. 1.

The first portions 1602 of linkages 1600*a*, 1600*b* are rotatably positioned on the first flange 1234 of the linkage bar 1230 of the linkage block 1200, and the first portions 1602 of linkages 1610*a*, 1610*b* are rotatably positioned on the second flange 1236 of the linkage bar 1230 of the linkage block 1200. The linkages can optionally be rotatably coupled to the flanges of the linkage bar 1230. The first portions of each of linkages 1600*a*, 1600*b*, 1610*a*, 1610*b* includes a flange opening 1620 that is configured to receive a portion of first or second flanges 1234, 1236 of linkage bar 1230. In one non-limiting arrangement, as illustrated in FIGS. 1-2, the first and second linkages 1600*a*, 1600*b* rotatably engage and/or are rotatably coupled to the first flange 1234 of the linkage bar 1230 of the linkage block 1200 along the same rotation axis, and the third and fourth linkages 1610*a*, 1610*b* rotatably engage and/or are rotatably coupled to the second flange 1236 of the linkage bar 1230 of the linkage block 1200 along the same rotation axis. In one non-limiting embodiment, the same rotation axis is shared by all four linkages when rotatably engage and/or are rotatably coupled to the linkage bar 1230 of the linkage block 1200. In another non-limiting embodiment, the same rotation axis is shared by all four linkages when connected to the linkage bar 1230 of the linkage block 1200, and the rotation axis is along the central longitudinal axis of the linkage bar 1230. As illustrated in FIGS. 1-2, at least a portion of the first and second linkages 1600*a*, 1600*b* overlie one another along the rotation axis of the linkages, and at least a portion of the third and fourth linkages 1610*a*, 1610*b* overlie one another along the rotation axis of the linkages. As illustrated in FIGS. 1-2, linkage 1600*b* is located closer to linkage opening 1238 of linkage body 1232 than linkage

1600*a*. Likewise, linkage 1610*b* is located closer to linkage opening 1238 of linkage body 1232 than linkage 1610*a*.

The second portions 1604 of linkages 1600*a*, 1610*b* are configured to engage, rotatably engage and/or be rotatably coupled to the first endplate 1400, and the second portions 1604 of linkages 1600*b*, 1610*a* are configured to engage, rotatably engage and/or be rotatably coupled to the second endplate 1500.

The second portions 1604 of linkages 1600*a*, 1610*b* and the second portions 1604 of linkages 1600*b*, 1610*a* include a pin opening 1630 that is configured to receive a pin 1640. The pin 1640 can be rigidly connected in the pin opening 1630 of one or more or all of linkages 1600*a*, 1610*b*, 1600*b*, 1610*a*, rotatably engage the pin opening 1630 of one or more or all of linkages 1600*a*, 1610*b*, 1600*b*, 1610*a*, or be rotatably connected to the pin opening 1630 of one or more or all of linkages 1600*a*, 1610*b*, 1600*b*, 1610*a*. In one non-limiting arrangement, pin 1640 is rigidly connected in the pin opening 1630 of each linkage 1600*a*, 1610*b*, 1600*b*, 1610*a*. In another non-limiting arrangement, pin 1640 rotatably engages the pin opening 1630 of each linkage 1600*a*, 1610*b*, 1600*b*, 1610*a*, and may or may not be rotatably connected to the pin opening 1630 of each linkage 1600*a*, 1610*b*, 1600*b*, 1610*a*.

Referring again to FIG. 13, the bottom structures on the first endplate 1400 and second endplate 1500 are mirror images of one another about the central longitudinal axis of the expandable prosthetic device 1000. As such, the bottom structures of the second endplate 1500 as best illustrated in FIG. 13 will be described in detain; however, it will be appreciated that the first endplate has similar structures and similarly functioning structures unless stated otherwise.

The bottom surface of the second endplate 1500 includes pivot openings 1522, 1524 that are positioned near, but rearwardly of the distal end of the second endplate 1500. The pivot openings 1522, 1524 are configured to receive a portion of pin 1640 that is positioned on linkages 1600*a*, 1610*a* respectively. The pin 1640 can be rigidly positioned in or rotatably positioned in pivot openings 1522, 1524.

Also positioned on the bottom surface of the second endplate 1500 is a downwardly extending guide flange 1530 that is positioned on one side of the second endplate 1500. As illustrated in FIG. 13, the bottom surface of the first endplate 1400 has a downwardly extending guide flange 1430 that is positioned on one side of the first endplate 1400 that is opposite from the side of the guide flange 1530 on the side of the second endplate 1500. The inner surface of the guide flange 1530 includes a guide slot 1532. Guide slot 1532 is configured to slidably receive block ramp 1172 on drive block 1100, and guide slot 1432 on the inner surface of guide flange 1430 is configured to slidably receive block ramp 1170 on drive block 1100. As illustrated in FIG. 13, both the guide flange and guide slot have an arcuate shape or profile. The guide flange and guide slot arrangement are used to facilitate in guiding the movement of the first and second endplates relative to the drive block 1100 as the expandable prosthetic device 1000 moves from the fully closed or collapsed position to the fully expanded or open position.

The distal portion of the linkage housing 1210 can optionally include a sloped surface on the top and/or bottom portions of the linkage housing 1210 as illustrated in FIG. 13. In one optional configuration, the sloped surface on the top and/or bottom portions of the linkage housing 1210 are configured to facilitate in causing the distal ends of the first and second endplates 1400, 1500 to begin separating from one another as the drive screw is initially rotated to cause the linkage block 1200 to move toward the drive block 1100 as the expandable prosthetic device 1000 initially from the fully closed or collapsed position to the fully expanded or open position. As the linkage block 1200 continues to move toward the drive block 1100, the first and second endplates 1400, 1500 disengage contact from the linkage housing 1210.

As illustrated in FIGS. 9 and 13, the second endplate 1500 includes a recessed side portion 1540 that is configured to receive a portion of guide flange 1430 in the first endplate 1400 when the expandable prosthetic device 1000 is in the fully closed or collapsed position. Likewise, the first endplate 1400 includes a recessed side portion 1440 that is configured to receive a portion of guide flange 1530 in the second endplate 1500 when the expandable prosthetic device 1000 is in the fully closed or collapsed position.

As illustrated in FIG. 13, the proximal end of the drive block 1100 includes two pin slots 1180, 1182. Pin slot 1180 is illustrated as being located closer to the bottom surface of drive block 1100 than pin slot 1182; however, this is not required. The proximal end of the first and second endplates include a plate slot 1452, 1552 on flanges 1450, 1550 respectively. The plate slots 1452, 1552 have an elongated cross-sectional shape (e.g., oval, discorectangle, obround, etc.), whereas the pin slots 1180, 1182 have a generally circular cross-sectional shape; however, this is not required. The cross-sectional area of the plate slots 1452, 1552 is greater than the cross-sectional shape of the pin slots 1180, 1182; however, this is not required. As can be appreciated, the shapes and sizes of the plate slots 1452, 1552 and the pin slots 1180, 1182 can be reversed. The plate slots 1452, 1552 and the pin slots 1180, 1182 are configured to receive a guide pin 1700 that is configured to limit the amount of movement of the proximal end of the drive block 1100 relative to the first and/or second endplates 1400, 1500 as the expandable interbody device 1000 moves from the fully closed or collapsed position to the fully open or expanded position. The plate slots 1452, 1552 are generally larger than pin slots 1180, 1182 to allow more movement of the guide pins 1700 within plate slots 1452, 1552 than within pin slots 1180, 1182.

The proximal portion of the drive block 1100 optionally includes a sloped surface 1190 and the top and/or bottom sides of the drive block 1100. The sloped surface 1190, when used, facilitates in causing the proximal ends of the first and second endplates 1400, 1500 to separate from one another as the drive block 1100 moves toward the linkage block 1200 as the drive screw 1300 is rotated and the expandable prosthetic device 1000 moves form the fully closed or collapsed position to the fully open or expanded position.

As illustrated in FIGS. 1-13, the first and second endplates 1400, 1500 are not pivotally connected together.

One or more or all of the components of the expandable prosthetic device 1000 can be partially or fully formed of a metal alloy. In one non-limiting embodiment, a portion or all of the one or more or all of the components of the expandable prosthetic device is formed of a metal alloy selected from a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) refractory metal alloy, or l) metal alloy that includes at least 5 awt. % rhenium. The material used to form the different components of the expandable prosthetic device 1000 can be the same or different.

One or more portions of the outer surface of the expandable prosthetic device 1000 can be coated with an enhancement layer. Non-limiting enhancement layers include chromium nitride (CrN), diamond-like carbon (DLC), titanium nitride (TiN), titanium oxynitride or titanium nitride oxide (TiNO$_x$), zirconium nitride (ZrN), zirconium oxide (ZrO$_2$), zirconium oxynitride (ZrN$_x$O$_y$) [e.g., cubic ZrN:O, cubic ZrO$_2$:N, tetragonal ZrO$_2$:N, and monoclinic ZrO$_2$:N phase coatings], oxyzirconium-nitrogen-carbon (ZrNC), zirconium OxyCarbide (ZrOC), and combinations of such coatings. The one or more enhancement layers, when used, can be optionally applied to a portion or all of the outer surface of the expandable prosthetic device 1000 by use of a physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process. The thickness of the enhancement layer, when used, is greater than 1 nanometer.

The expandable prosthetic device 1000 can optionally be partially or fully be coated with and/or include one or more agents.

One or more portions of the expandable prosthetic device 1000 can optionally include a marker material that facilitates enabling the expandable prosthetic device 1000.

In use, the first and second endplates 1400, 1500 of the expandable interbody device 1000 begin at a minimum distance from each other (a minimum "height") in a closed position, as illustrated in FIGS. 7-12. A rotation tool (not illustrated) is inserted into the screw opening 1320 of the head 1310 of the drive screw 1300.

The drive screw 1300 is rotated within the drive block opening 1120 and the linkage housing 1210 to cause the linkage block 1200 and the drive block 1100 to move toward one another. During rotation of the drive screw 1300, the head 1310 of the drive screw 1300 does not move axially along the longitudinal axis of the drive block. In one non-limiting arrangement, a portion of the drive screw extends outwardly from the distal end of the linkage housing 1210 when the expandable interbody device 1000 is in the fully open or expanded position as illustrated in FIG. 3. In another non-limiting embodiment, the head 1310 of the drive screw 1300 does not extend outwardly from the proximal end of the drive block opening 1120.

As the linkage block 1200 and the drive block 1100 move toward one another during the rotation of the drive screw 1300, the relative angles of the longitudinal axes of each of the linkages 1600a, 1600b and linkages 1610a, 1610b increase with respect to the central axis of the linkage block 1200. The increasing relative angles of the longitudinal axes of the linkages 1600a, 1600b and linkages 1610a, 1610b with respect to the central axis of the linkage block 1200 cause the distal ends of the first and second endplates 1400, 1500 to move away from each other until the expandable interbody device 1000 reaches the fully open or expanded position as illustrated in FIGS. 1-6. Thus, rotation of the drive screw 1300 can simultaneously cause movement of the linkage block 1200 relative to the drive block 1100 and movement of the first endplate 1400 relative to the second endplate 1500.

As the first and second endplates 1400, 1500 move away from each other and away from the drive block 1100, the guide slots 1432, 1532 slides along the guide flanges 1430, 1530 to create a desired specific movement path of the first and second endplates 1400, 1500 relative to the drive block 1100 as the expandable interbody device 1000 moves from the fully closed or collapsed position to the fully open or expanded position thereby causing the angle between the top sides of the first and second endplates 1400, 1500 to increase. The angle between the first sides 1412, 1512 of the first and second endplates 1400, 1500 is also referred to as the lordosis of the expandable interbody device 1000.

A number of implementations have been described. Nevertheless, it will be understood that various modifications may be made without departing from the spirit and scope of the claims. Accordingly, other implementations are within the scope of the following claims.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall therebetween.

What is claimed:

1. An expandable interbody device; said expandable interbody device comprising: a drive block; said drive block includes a drive block opening; a linkage block; said linkage block includes a linkage housing and a linkage bar; said linkage bar is at least partially positioned in said linkage housing; said linkage block includes a linkage block opening; a block engagement arrangement; a drive screw; said drive screw includes a head and body portion; said drive screw at least partially positioned within said drive block opening and at least partially position in said linkage block opening; said drive screw rotatable relative to said drive block opening and said linkage block opening; said head is rotatably positioned in within said drive block opening; a first endplate and a second endplate; said first endplate includes a first endplate engagement arrangement; said second endplate includes a second endplate engagement arrangement; said first and second endplate engagement arrangements are configured to engage with said block engagement arrangement; and, a first linkage arrangement; said first linkage arrangement includes first and second linkages; said first linkage is rotatably coupled to said linkage block and engages said first endplate; said second linkage is rotatably coupled to said linkage block and engages said second endplate; wherein rotation of said drive screw causes one or more of I) movement of at least one of said linkage block and said drive block, II) movement of at least one of said first endplate and said second endplate, and/or III) said first and/or second endplate engagement arrangements moving relative to at least one of said linkage block and said drive block; and wherein said engagement of said block engagement arrangement with said first endplate engagement and said second endplate engagement is configured to at least partially guide movement of said first and/or second endplates relative to said drive block and/or said linkage block during rotation of said drive screw, wherein said first linkage of said first linkage arrangement rotatably engages said first endplate; second linkage of said first linkage arrangement rotatably engage said second endplate; said first linkage of said first linkage arrangement is configured to engage with said first endplate, but is not connected to said first endplate; said second linkage of said first linkage arrangement is configured to engage with said second endplate, but is not connected to said second endplate.

2. The expandable interbody device as defined in claim 1, wherein said block engagement arrangement is at least partially positioned on said drive block.

3. The expandable interbody device as defined in claim 1, wherein said block engagement arrangement includes at least one of a slot, protrusion, rib, rail, or groove; said first endplate engagement arrangement includes at least one of a slot, protrusion, rib, rail, or groove; said second endplate engagement arrangement includes at least one of a slot, protrusion, rib, rail, or groove.

4. The expandable interbody device as defined in claim 1, wherein said block engagement arrangement is configured to slidably engage with said first endplate engagement arrangement as said first end plate moves relative to said block engagement arrangement; said block engagement arrangement is configured to slidably engage with said second endplate engagement arrangement as said second end plate moves relative to said block engagement arrangement.

5. The expandable interbody device as defined in claim 1, wherein said drive screw is rotatably coupled within said drive block opening; said drive screw is not threadedly coupled to said drive block; said drive screw is threadedly coupled within said linkage block opening.

6. The expandable interbody device as defined in claim 1, wherein said first endplate engagement arrangement includes a first endplate engagement member; said block engagement arrangement includes a first block engagement member; said first endplate engagement member is slidably engageable with said first block engagement member.

7. The expandable interbody device as defined in claim 1, wherein said first endplate and said second endplate each include first and second ends; said first end of said first endplate and said second endplate are each positioned at one end of said expandable interbody device and said second end of said first endplate and said second endplate are each positioned at an opposite end of said expandable interbody device; said first end of said first endplate and said second endplate change in spacing from one another as said expandable interbody device moved between an open and closed position; said second end of said first endplate and said second endplate change in spacing from one another as said expandable interbody device moved between an open and closed position.

8. The expandable interbody device as defined in claim 1, wherein each of said drive block, said first endplate and said second endplate includes a graft window; said graft window of said drive block, said first endplate and said second endplate are at least partially aligned with one another when said expandable interbody device is in a closed position and in an open position.

9. The expandable interbody device as defined in claim 1, further including a second linkage arrangement; said second linkage arrangement is positioned on an opposite side of said expandable interbody device from said first linkage arrangement; said second linkage arrangement includes first and second linkages; said second linkage of said second linkage arrangement is rotatably coupled to said linkage block and engages said first endplate; said second linkage of said second linkage arrangement is rotatably coupled to said linkage block and engages said second endplate.

10. The expandable interbody device as defined in 9, wherein said first linkage of said second linkage arrangement rotatably engages said first endplate; second linkage of said second linkage arrangement rotatably engages said second endplate; said first linkage of said second linkage arrangement is configured to engage with said first endplate, but is not connected to said first endplate; said second linkage of said second linkage arrangement is configured to engage with said second endplate, but is not connected to said second endplate.

11. The expandable interbody device as defined in claim 1, wherein one or more of said first endplate and said second endplate includes a micro-textured surface and/or one or more teeth.

12. The expandable interbody device as defined in claim 1, wherein said drive block and said linkage block are configured to both move along a longitudinal axis of said expandable interbody device and both move relative to said first and second endplates when said drive screw is rotated.

13. The expandable interbody device as defined in claim 1, wherein said drive block includes a pin slot, and said first and/or second endplates includes a plate slot, and wherein said pin slot and said plate slot is configured to receive a guide pin that is configured to limit the amount of movement of a proximal end of said drive block relative to said first and/or second endplates as said expandable interbody device moves from a fully closed to a fully open position.

14. The expandable prosthetic device as defined in claim 1, wherein at least a portion of said expandable prosthetic device includes one or more metal alloys selected from the group consisting of a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) refractory metal alloy, or l) metal alloy that includes at least 5 awt. % rhenium.

15. The expandable prosthetic device as defined in claim 1, wherein one or more portions of said expandable prosthetic device includes an enhancement layer; said enhancement layer includes one or more include chromium nitride (CrN), diamond-like carbon (DLC), titanium nitride (TiN), titanium oxynitride or titanium nitride oxide (TiNO$_x$), zirconium nitride (ZrN), zirconium oxide (ZrO$_2$), zirconium oxynitride (ZrN$_x$O$_y$), oxyzirconium-nitrogen-carbon (ZrNC), and/or zirconium OxyCarbide (ZrOC).

16. A method for using an expandable prosthetic device comprising: providing said expandable prosthetic device; said expandable prosthetic device comprises: a drive block; said drive block includes a drive block opening; a linkage block; said linkage block includes a linkage housing and a linkage bar; said linkage bar is at least partially positioned in said linkage housing; said linkage block includes a linkage block opening; a block engagement arrangement; a drive screw; said drive screw includes a head and body portion; said drive screw at least partially positioned within said drive block opening and at least partially position in said linkage block opening; said drive screw rotatable relative to said drive block opening and said linkage block opening; said head is rotatably positioned in within said drive block opening; a first endplate and a second endplate; said first endplate includes a first endplate engagement arrangement; said second endplate includes a second endplate engagement arrangement; said first and second endplate engagement arrangements are configured to engage with said block engagement arrangement; and, a first linkage arrangement; said first linkage arrangement includes first and second linkages; said first linkage is rotatably coupled to said linkage block and engages said first endplate; said second linkage is rotatably coupled to said linkage block and engages said second endplate; wherein rotation of said drive screw causes one or more of I) movement of at least one of said linkage block and said drive block, II) movement of at least one of said first endplate and said second endplate, and/or III) said first and/or second endplate engagement arrangements moving relative to at least one of said linkage block and said drive block; and wherein said engagement of said block engagement arrangement with said first endplate engagement and said second endplate engagement is configured to at least partially guide movement of said first and/or second endplates relative to said drive block and/or said linkage block during rotation of said drive screw; inserting said expandable prosthetic device into a patient; and causing said drive screw to rotate which results in A) movement of said linkage block relative to said drive block and B) movement of said first endplate relative to said second endplate, wherein said first linkage of said first linkage arrangement rotatably engages said first endplate; second linkage of said first linkage arrangement rotatably engage engages said second endplate; said first linkage of said first linkage arrangement is configured to engage with said first endplate, but is not connected to said first endplate: said second linkage of said first linkage arrangement is configured to engage with said second endplate, but is not connected to said second endplate.

17. The method as defined in claim 16, wherein said block engagement arrangement is at least partially positioned on said drive block.

18. The method as defined in claim 16, wherein said block engagement arrangement includes at least one of a slot, protrusion, rib, rail, or groove; said first endplate engagement arrangement includes at least one of a slot, protrusion, rib, rail, or groove; said second endplate engagement arrangement includes at least one of a slot, protrusion, rib, rail, or groove.

19. The method as defined in claim 16, wherein said block engagement arrangement is configured to slidably engage with said first endplate engagement arrangement as said first end plate moves relative to said block engagement arrangement; said block engagement arrangement is configured to slidably engage with said second endplate engagement arrangement as said second end plate moves relative to said block engagement arrangement.

20. The method as defined in claim 16, wherein said drive screw is rotatably coupled within said drive block opening; said drive screw is not threadedly coupled to said drive block; said drive screw is threadedly coupled within said linkage block opening.

21. The method as defined in claim 16, wherein said first endplate engagement arrangement includes a first endplate engagement member; said block engagement arrangement includes a first block engagement member; said first endplate engagement member is slidably engageable with said first block engagement member.

22. The method as defined in claim 16, wherein said first endplate and said second endplate each include first and second ends; said first end of said first endplate and said second endplate are each positioned at one end of said expandable interbody device and said second end of said first endplate and said second endplate are each positioned at an opposite end of said expandable interbody device; said first end of said first endplate and said second endplate change in spacing from one another as said expandable interbody device moved between an open and closed position; said second end of said first endplate and said second endplate change in spacing from one another as said expandable interbody device moved between an open and closed position.

23. The method as defined in claim 16, wherein each of said drive block, said first endplate and said second endplate includes a graft window; said graft window of said drive block, said first endplate and said second endplate are at least partially aligned with one another when said expandable interbody device is in a closed position and an open position.

24. The method as defined in claim 16, further including a second linkage arrangement; said second linkage arrangement positioned on an opposite side of said expandable interbody device from said first linkage arrangement; said second linkage arrangement includes first and second linkages; said second linkage of said second linkage arrangement is rotatably coupled to said linkage block and engages said first endplate; said second linkage of said second linkage arrangement is rotatably coupled to said linkage block and engages said second endplate.

25. The method as defined in 24, wherein said first linkage of said second linkage arrangement rotatably engages said first endplate; second linkage of said second linkage arrangement rotatably engages said second endplate; said first linkage of said second linkage arrangement is configured to engage with said first endplate, but is not connected to said first endplate; said second linkage of said second linkage arrangement is configured to engage with said second endplate, but is not connected to said second endplate.

26. The method as defined in claim 16, wherein one or more of said first endplate and said second endplate includes a micro-textured surface and/or one or more teeth.

27. The method as defined in claim 16, wherein said drive block and said linkage block are configured to both move along a longitudinal axis of said expandable interbody device and both move relative to said first and second endplates when said drive screw is rotated.

28. The method as defined in claim 16, wherein said drive block includes a pin slot, and said first and/or second endplates includes a plate slot, and wherein said pin slot and said plate slot is configured to receive a guide pin that is configured to limit the amount of movement of a proximal end of said drive block relative to said first and/or second endplates as said expandable interbody device moves from a fully closed to a fully open position.

29. The method as defined in claim 16, wherein at least a portion of said expandable prosthetic device includes one or more metal alloys selected from the group consisting of a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) refractory metal alloy, or l) metal alloy that includes at least 5 awt. % rhenium.

30. The method as defined in claim 16, wherein one or more portions of said expandable prosthetic device includes an enhancement layer; said enhancement layer includes one or more include chromium nitride (CrN), diamond-like carbon (DLC), titanium nitride (TiN), titanium oxynitride or titanium nitride oxide ($TiNO_x$), zirconium nitride (ZrN), zirconium oxide ($ZrO_2$), zirconium oxynitride ($ZrN_xO_y$), oxyzirconium-nitrogen-carbon (ZrNC), and/or zirconium OxyCarbide (ZrOC).

\* \* \* \* \*